(12) United States Patent
Remirez et al.

(10) Patent No.: US 10,737,398 B2
(45) Date of Patent: Aug. 11, 2020

(54) CONTINUUM DEVICES AND CONTROL METHODS THEREOF

(71) Applicant: Vanderbilt University, Nashville, TN (US)

(72) Inventors: Andria A. Remirez, Nashville, TN (US); Daniel Caleb Rucker, Knoxville, TN (US); Robert James Webster, III, Nashville, TN (US)

(73) Assignee: Vanderbilt University, Nashville, TN (US)

(*) Notice: Subject to any disclaimer, the term of this patent is extended or adjusted under 35 U.S.C. 154(b) by 460 days.

(21) Appl. No.: 14/491,223

(22) Filed: Sep. 19, 2014

(65) Prior Publication Data

US 2016/0016319 A1    Jan. 21, 2016

Related U.S. Application Data

(63) Continuation-in-part of application No. 13/808,994, filed as application No. PCT/US2011/038539 on May 31, 2011, now Pat. No. 9,289,899.
(Continued)

(51) Int. Cl.
*G06F 19/00* (2018.01)
*B25J 18/06* (2006.01)
(Continued)

(52) U.S. Cl.
CPC .............. *B25J 18/06* (2013.01); *A61B 34/30* (2016.02); *A61B 34/71* (2016.02); *B25J 9/104* (2013.01); *A61B 2034/306* (2016.02)

(58) Field of Classification Search
CPC ........ A61B 19/2203; A61B 2019/2211; A61B 2017/00477; A61B 19/5244; A61B 2019/2242; A61B 2019/5261; A61B 18/1445; A61B 2019/082; A61B 2019/2246; A61B 2019/461; A61B 2017/003; A61B 2019/2223; A61B 2019/2276; A61B 2019/2284; A61B 2019/2292; A61B 2019/5259; A61B 2017/00323; A61B 5/0066; A61B 5/418; Y10S 901/38; Y10S 901/28; B25J 9/104; B25J 17/00; B25J 18/06; B25J 9/0015; B25J 9/10; B25J 9/0006; B25J 9/0078; B25J 9/046; B25J 9/06; B25J 9/1075;
(Continued)

(56) References Cited

U.S. PATENT DOCUMENTS 3,868,956 A * 3/1975 Alfidi ................. A61B 17/22
128/899
5,317,952 A    6/1994 Imegga
(Continued)

OTHER PUBLICATIONS

Bergou et al., "Discrete elastic rods", ACM Trans. Graph. (2008) 27(3). (12 pages).
(Continued)

*Primary Examiner* — Ronnie M Mancho
(74) *Attorney, Agent, or Firm* — Nixon Peabody LLP

(57) ABSTRACT

Continuum robots and similar devices and methods and systems for controlling such devices are provided. The devices can include rods comprising strips, that are pre-curved, or both. Also provided is a system and method for modeling and controlling the configuration and operation of such devices.

10 Claims, 27 Drawing Sheets

Related U.S. Application Data

(60) Provisional application No. 61/362,353, filed on Jul. 8, 2010, provisional application No. 61/879,727, filed on Sep. 19, 2013.

(51) Int. Cl.
  *B25J 9/10* (2006.01)
  *A61B 34/30* (2016.01)
  *A61B 34/00* (2016.01)

(58) Field of Classification Search
  CPC . B25J 9/16; B25J 9/1615; B25J 9/1625; B25J 9/1633; B25J 9/1635; B25J 9/1694; A61M 25/0147; A61M 25/0133; H02K 26/00; H02K 7/003; Y10T 74/20329; A61F 2002/704; G05B 2219/39186; G05B 2219/39457; G05B 2219/40273; G05B 2219/40279; G05B 2219/40324
  USPC .................. 700/245, 262, 250, 260, 261
  See application file for complete search history.

(56) References Cited

U.S. PATENT DOCUMENTS

| | | | |
|---|---|---|---|
| 6,071,274 A * | 6/2000 | Thompson | A61B 18/1492 604/528 |
| 6,332,881 B1 * | 12/2001 | Carner | A61B 18/1402 606/41 |
| 6,986,739 B2 | 1/2006 | Warren et al. | |
| 8,460,236 B2 | 6/2013 | Roelle et al. | |
| 8,672,837 B2 | 3/2014 | Roelle et al. | |
| 2003/0018388 A1 | 1/2003 | Comer | |
| 2003/0109778 A1 * | 6/2003 | Rashidi | A61B 18/1492 600/374 |
| 2005/0028237 A1 | 2/2005 | Greenhill et al. | |
| 2009/0024141 A1 | 1/2009 | Stahler et al. | |
| 2009/0123111 A1 | 5/2009 | Udd | |
| 2009/0138025 A1 * | 5/2009 | Stahler | 606/130 |
| 2009/0182436 A1 | 7/2009 | Ferrara | |
| 2010/0263470 A1 | 10/2010 | Bannasch et al. | |
| 2011/0319815 A1 | 12/2011 | Roelle et al. | |
| 2012/0010628 A1 | 1/2012 | Cooper et al. | |
| 2013/0165945 A9 | 6/2013 | Roelle et al. | |

OTHER PUBLICATIONS

Buckingham et al., "Reaching the unreachable—Snake arm robots", Retrieved on Aug. 27, 2013, from http://www.ocrobotics.com/downloads/EngineeringNov04.pdf (1 page).

Camarillo et al., "Mechanics modeling of tendon-driven continuum manipulators", IEEE Transactions on Robotics (2008) 24(6): 1262-1273.

Chirikjian et al., "A modal approach to hyper-redundant manipulator kinematics", IEEE Trans. Robot. Auton. (1994) 10(3): 343-353.

Chirikjian, "Hyper-redundant manipulator dynamics: A continuum approximation", Adv Robot (1995) 9(3): 217-243.

Chirikjian et al., "Kinematically optimal hyper-redundant manipulator configurations", IEEE Trans. Robot. Autom. (1995) 11(6): 794-806.

Davis et al., "A model for the embedded tendon control of a slender three-dimensional flexible robot link", Dynamics and Control (1994) 4(2): 185-208.

Gravagne, "Design, analysis and experimentation: The fundamentals of continuum robotic manipulators", Ph.D. Dissertation, Dept Elect Comput Eng, Clemson Univ. (2002). (135 pages).

Gravagne et al., "Large deflection dynamics and control for planar continuum robots", IEEE/ ASME Trans. Mechatron (2003) 8: 299-307.

Gravagne et al., "Manipulability, force, and compliance analysis for planar continuum robots", IEEE Tran. Robot. Autom (2002) 18(3): 263-273.

International Search Report and the Written Opinion dated Feb. 9, 2012 in PCT Application No. PCT/US2011/038539, international filing date May 31, 2011. (9 pages).

Jones et al., "Three-dimensional statics for continuum robots", Proc. IEEE/RSJ Inc. Conf. Intell. Robots Syst. (2009): 2659-2664.

Li et al., "Design of continuous backbone, cable-driven robots", ASME J Mech Design (2002) 124(2): 265-271.

Murray et al., "A mathematical introduction to robotic manipulation", CRC Press: Boca Raton (1994). (474 pages).

Robinson et al., "Continuum robots—A state of the art", Proc IEEE Int Conf Robot Autom (1999): 2849-2854.

Rucker et al., "A geometrically exact model for externally loaded concentric-tube continuum robots", IEEE Trans Robot (2010) 26(5): 769-780.

Rucker et al., "Exact mechanics of continuum robots with general tendon routing", Proc 12th Int Symp Exp Robot (2010): 1-10.

Shampine, "Solving hyperbolic PDE's in MATLAB", Appl. Numer. Anal. Comput. Math. (2005) 2(3): 346-358.

Simaan et al., "Steerable continuum robot design for cochlear implant surgery", Proc. IEEE Int. Conf. Robot. Autom. (2010): 36-38.

Trivedi et al., "Soft robotics: Biological inspiration, state of the art, and future research", Appl. Bionics Biomech (2008) 5(3): 99-117.

Webster et al., "Design and kinematic modeling of constant curvature continuum robots: A review", Int J Robot Res (2010 29: 1661-1683.

Wilson et al., "The mechanics of positioning highly flexible manipulator limbs", J Mech Transmiss Autom Design (1989) 111: 232-237.

Xu et al., "Analytic formulation for kinematics, statics and shape restoration of multi-backbone continuum robots via elliptic integrals", ASME J Mech Robot (2010) 2(1): 011 006-1-011 006-13.

Xu et al., "Intrinsic wrench estimation and its performance index for multisegment continuum robots", IEEE Trans Robot (2010) 26(3): 555-561.

* cited by examiner

CONTINUUM DEVICES AND CONTROL METHODS THEREOF

CROSS-REFERENCE TO RELATED APPLICATIONS

This application claims the benefit of Provisional Application Ser. No. 61/879,727, entitled "FLEXIBLE INSTRUMENT WITH PRE-CURVED ELEMENTS" and filed Sep. 19, 2013. This application is also a continuation-in-part of U.S. Non-Provisional application Ser. No. 13/808,994, entitled "CONTINUUM ROBOTS AND CONTROL THEREOF" and filed Feb. 5, 2013, which is a National Stage of International Application Serial No. PCT/US2011/38539, entitled "CONTINUUM ROBOTS AND CONTROL THEREOF" and filed May 31, 2011, which claims the benefit of Provisional Application Ser. No. 61/362,353, entitled "CONTINUUM ROBOTS AND CONTROL THEREOF" and filed Jul. 8, 2010. The above-identified documents are each herein incorporated by reference in their entirety.

GOVERNMENT LICENSE RIGHTS

This invention was made with government support under contract/grant no. IIS-I054331 awarded by National Science Foundation. The government has certain rights in the invention

FIELD OF THE INVENTION

The present invention relates to flexible instruments, and more specifically to apparatus and methods for configuring and operating such flexible instruments.

BACKGROUND

Continuum robots offer a number of potential advantages over traditional rigid link robots in certain applications, particularly those involving reaching through complex trajectories in cluttered environments or where the robot must compliantly contact the environment along its length. The inherent flexibility of continuum robots makes them gentle to the environment, able to achieve whole arm manipulation, and gives rise to a unique form of dexterity the shape of the robot is a product of both actuator and externally applied forces and moments. However, existing designs for continuum robots provide a limited range of motion and thus limit their usefulness.

DETAILED DESCRIPTION

Figure 1:
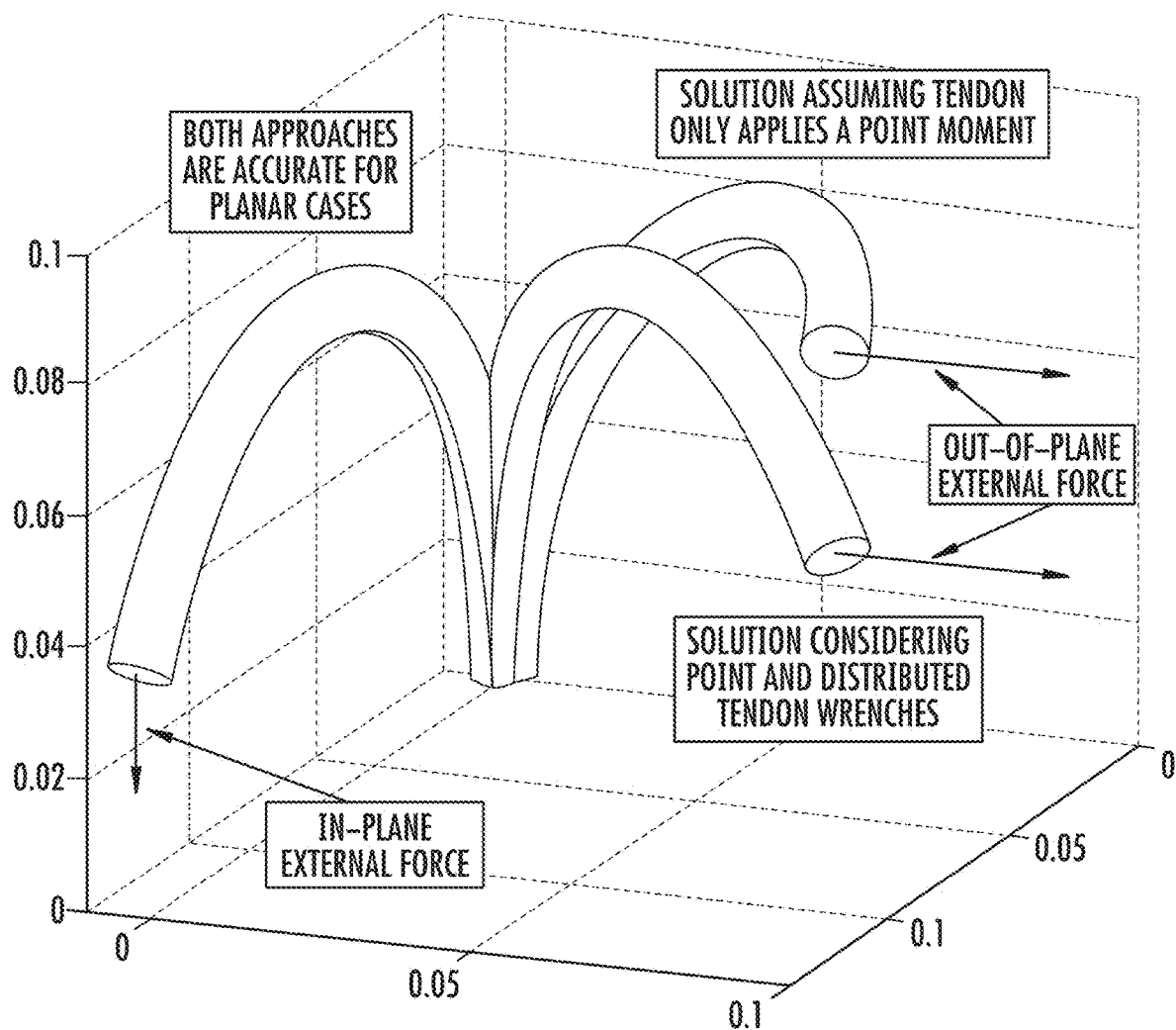
FIG. 1 is an illustration of the results of simulations of a continuum robot with single, straight, tensioned tendons with in-plane and out-of-plane forces applied at the tip.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

I. Introduction

The various embodiments of the invention provide systems and methods for the control of continuum robots and similar flexible devices and instruments. Although, the discussion of the various embodiments will be in terms of wire-actuated ("tendons") or rod-actuated continuum robots, this is solely for ease of illustration. Accordingly, the various aspects of the invention can be utilized with any type of wire-actuated or rod-actuated device or instrument.

II. Low Stiffness Elements

One aspect of the various embodiments is directed to deformation or manipulation of some type of elastic structure using wires or string under tension (i.e., tendons or other elements with a lower stiffness than the elastic structure. These embodiments of the invention extend previous work on the Cosserat rod-based approach by taking into account not only the attachment point moment, but also the attachment point force and the distributed wrench that the tendon applies along the length of the elastic member. This approach couples the classical Cosserat string and rod models to express tendon loads in terms of the rod's kinematic variables.

The difference between this new coupled model and the point moment model for out of plane loads is shown in FIG. 1, and provide an experimental comparison of the two models described below. FIG. 1 is an illustration of the results of simulations of a continuum robot with single, straight, tensioned tendons with in-plane and out-of-plane forces applied at the tip. These illustrate the difference between the model proposed in this paper which includes distributed tendon wrenches, and the commonly used point moment approximation. For planar deformations and loads, the two models differ only by axial compression (which is small in most cases). However, for out of plane loads, the results differ significantly and including distributed wrenches enhances model accuracy (see Sec. V).

The various embodiments thus provide two new innovations over conventional methods. First, a new Cosserat rod-based model is provided for the spatial deformation of tendon actuated continuum robots under general external point and distributed wrench loads. This model is the first to treat the full effects of all of the tendon loads in a geometrically exact way for large 3D deflections. Second, the new model is the first to describe the mechanics of general tendon routing paths that need not run straight (along the undeformed robot configuration), as has been the case in prior prototypes. Thus, by providing a general model that can address most, if not all, types of tendon routing, this expands the design space and the set of shapes achievable for tendon-actuated robots.

In view of the foregoing, the various embodiments provide systems and methods for controlling continuum robots using exact models for the forward kinematics, statics, and dynamics and with general tendon routing experiencing external point and distributed loads. The models account for lance deformations due to bending, torsion, shear, and elongation. The static model is formulated as a set of nonlinear differential equations in standard form, and the dynamic model consists of a system of hyperbolic partial differential equations.

Using this approach, one can accurately predict the shape of a physical prototype with both straight and non-straight tendon routing paths and with external loading. With calibrated parameters, the mean tip error with respect to the total robot length can be significantly reduced as compared to conventional methods.

Figure 2A:
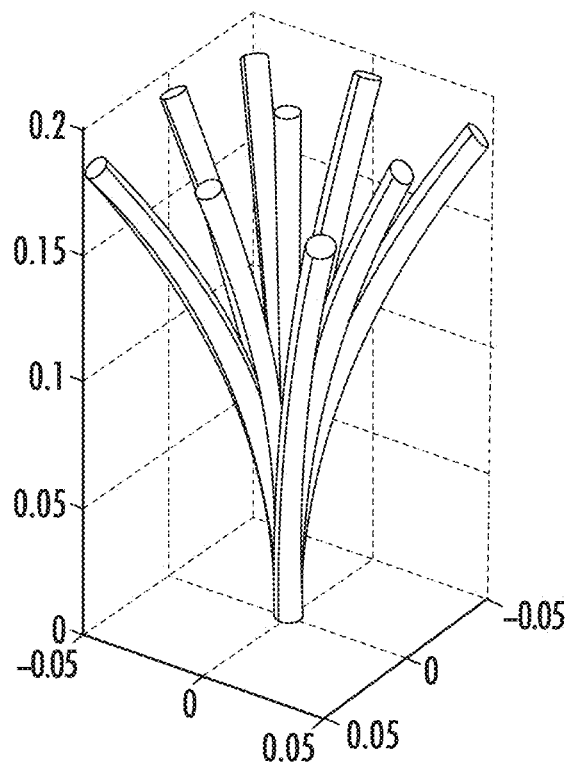
FIG. 2A is an illustration of an exemplary of robot shape/workspace modification for a robot with four straight tendons spaced at equal angles around its periphery.
Figure 2B:
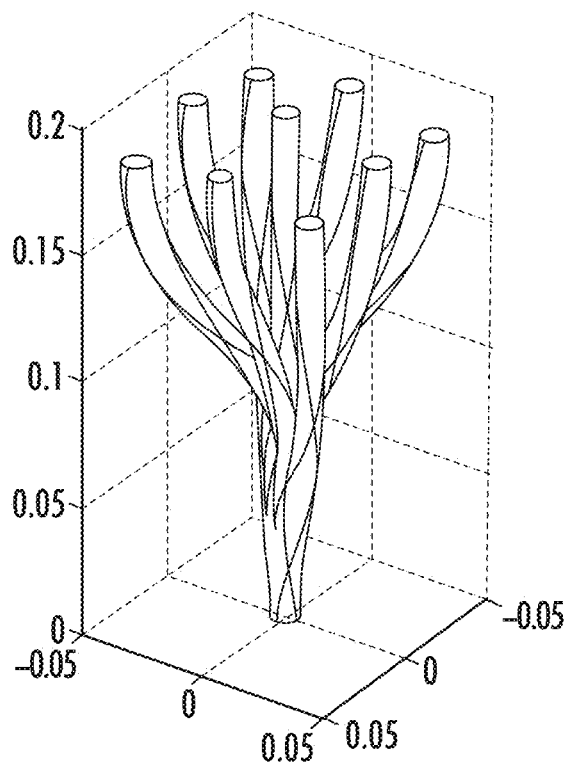
FIG. 2B is an illustration of an exemplary of robot shape/workspace modification for a robot with four helical tendons that each make one full revolution around the shaft.

As illustrated in FIGS. 2A and 2B, the design space of achievable robot shapes can be expanded by considering alternative tendon paths. For example, FIG. 2A is an illustration of an exemplary of robot shape/workspace modification for a robot with four straight tendons spaced at equal angles around its periphery. In contrast, FIG. 2B is an illustration of an exemplary of robot shape/workspace modification for a robot with four helical tendons that each make one full revolution around the shaft, in accordance with an embodiment of the invention. The two designs differ significantly in tip orientation capability, and the helical design may be better suited to some types of tasks, e.g. a planar industrial pick and place tasks or surgical tasks. Thus, such continuum robots could be used to enhance the capabilities of medical instruments introduced using an orifice or minimal incision and allow additional control during procedures. Some types of devices can include devices for procedures in the throat and airways (introduced via the mouth), in the colon (introduced via the anus), in the stomach (introduced via the mouth and traveling through the esophogus), in the abdomen (either via a transgastric natural orifice transluminal endoscopic surgery approach, or via an incision in the abdomen similar to normal laparoscopic surgery), in skull base surgery (entering via the nose), in the brain and subarachnoid (entering an area around the brain stem and center of the spine) spaces (entering via a craniotomy), or in the bladder and kidneys (entering via the urethra).

The models in accordance with the various embodiments of the invention therefore allow new quasi-static and/or dynamic control techniques for tendon-actuated continuum robots in the future. Furthermore, the inclusion of general external loads in tendon actuated continuum robot models is an important step forward for future practical applications, given their significant sag under self-weight and when carrying payloads. Additionally, such models can be used to address the issue of modeling static friction, and real-time computation of static and dynamic robot shape.

III. Model for a Simple Cosserat Rod

A. Elastic Structure Kinematics

In Cosserat-rod theory, a rod or other elastic structure is characterized by its centerline curve in space $p(s) \in \mathbb{R}^6$ and its material orientation, $R(s) \in SO(3)$ as functions of a reference parameter $s \in [0\ L]|$. Thus a homogeneous transformation can be used to describe the entire rod:

$$g(s) = \begin{bmatrix} R(s) & p(s) \\ 0 & 1 \end{bmatrix}$$

Kinematic variables v(s) and u(s) represent the linear and angular rates of change of g(s) with respect to s expressed in coordinates of the "body frame" g(s). Thus, the evolution of g(s) along s is defined by the following relationships;

$$\dot{R}(s) = r(s)\hat{u}(s),$$

$$\dot{p}(s) = r(s)v(s) \quad (1)$$

where, the dot denotes a derivative with respect to s, and the $\hat{}$ and $\vee$ operators are as defined by R. M. Murray, Z. Li, and S. S. Sastry in "A Mathematical Introduction to Robotic Manipulation." Boca Raton, Fla.: CRC Press, 1994. See also the Derivation Appendix for an explanation of these operators.

Letting the undeformed reference configuration of the rod be g*(s), where the z axis of R*(s) is chosen to be tangent to the curve p*(s). One could use the Frenet-Serret or Bishop's convention to define the x and y axes of R*(s), or, if the elastic structure has a cross section which is not radially symmetric, it is convenient to make the x and y axes align with the principal axes. The reference kinematic variables v* and u* can then be obtained by $$[v^{*T} u^{*T}]^T = (g^{*-1}(s)\dot{g}^*(s))^\vee,$$

If the reference configuration happens to be a straight cylindrical elastic structure with s as the arc length along it, then $v^* = [0\ 0\ 1]^T$ and $u^*(s) = [0\ 0\ 0]^T$.

B. Equilibrium Equations

Figure 3:
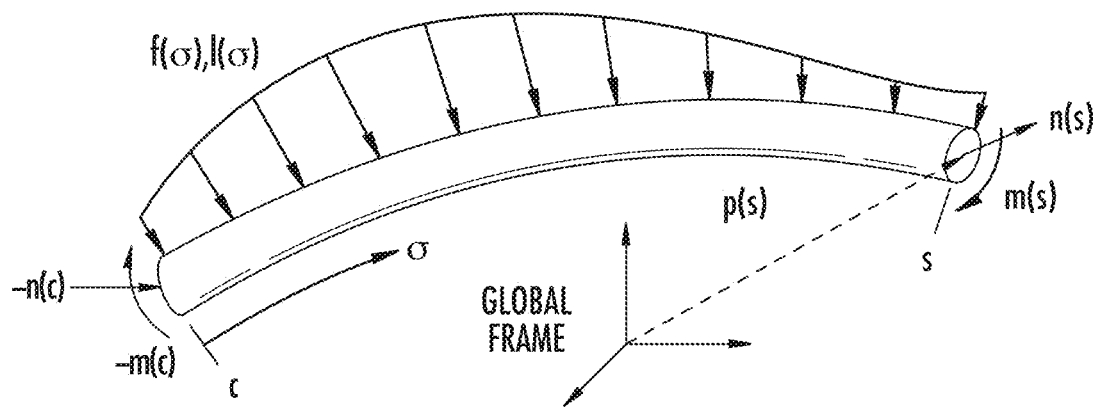
FIG. 3 is an illustration of an arbitrary section of rod from c to s subject to distributed forces and moments, showing the internal forces n and moments m.

One can the write the equations of static equilibrium for an arbitrary section of rod as shown in FIG. 3. The internal force and moment vectors (in global frame coordinates) are denoted by n and m, the applied force distribution per unit of s is f, and the applied moment distribution per unit of s is l. Taking the derivative of the static equilibrium conditions with respect to s, one arrives at the classic forms of the equilibrium differential equations for a special Cosserat rod, $$\dot{n}(s) + f(s) = 0, \quad (2)$$

$$\dot{m}(s) + \dot{p}(s) \times n(s) + l(s) = 0. \quad (3)$$

C. Constitutive Laws

The difference between the kinematic variables in the elastic structure's reference state and those in the deformed state can he directly related to various mechanical strains. For instance, transverse shear strains in the body-frame x and y directions correspond to $v_x - v_x^*$ and $v_y - v_y^*$ respectively, while axial elongation or stretch in the body-frame z direction corresponds to $v_z - v_z^*$. Similarly, bending strains about the local x and y axes are related to $u_x - u_x^*$ and $u_y - u_y^*$ respectively, while torsional strain about the local z axis is related to $u_z - u_z^*$.

One can use linear constitutive laws to map these strain variables to the internal forces and moments. Assuming that the x and y axes of g* are aligned with the principal axes of the cross section, one obtains $$n(s) = R(s)D(s)(v(s) - v^*(s)),$$

$$m(s) = R(s)C(s)(u(s) - u^*(s)), \quad (4)$$

where $$D(s) = \text{diag}(GA(s), GA(s), EA(s)), \text{ and}$$

$$C(s) = \text{diag}(EI_{xx}(s), EI_{yy}(s), EI_{xx}(s) + EI_{yy}(s)),$$

where A(s) is the area of the cross section, E(s) is Young's modulus, G(s) is the shear modulus, and $I_{xx}(s)$ and $I_{yy}(s)$ are the second moments of area of the tube cross section about the principal axes. (Note that $I_{xx}(s) + I_{yy}(s)$ is the polar moment of inertia about the centroid.) One can use these linear relationships here because they are notationally convenient and accurate for many continuum robots, but the Cosserat rod approach does not require it.

D. Explicit Model Equations

Equations (2) and (3) can then be written in terms of the kinematic variables using equation (4), their derivatives, and equation (1). This leads to the full set of differential equations shown below.

$$\dot{p} = Rv$$

$$\dot{R} = R\hat{u}$$

$$\dot{v} = \dot{v}^* - D^{-1}((\hat{u}D + \dot{D})(v - v^*) + R^T f)$$

$$\dot{u} = \dot{u}^* - C^{-1}((\hat{u}C + \dot{C})(u - u^*) + \hat{v}D(v - v^*) + R^T l) \quad (5)$$

Alternatively, an equivalent system can be obtained using m and n as state variables rather than v and u.

$$\dot{p} = R(D^{-1}R^T n + v^*)$$

$$\dot{R} = R(C^{-1}R^T m + u^*)\hat{}$$

$$\dot{n} = -f$$

$$\dot{m} = -\dot{p} \times n - l \quad (6)$$

Boundary conditions for a rod which is clamped at s=0 and subject to an applied force $F_l$ and moment $L_l$ at s=l would be $R(0) = R_0$, $p(0) = p_0$, $m(l) = L_l$, and $n(l) = F_l$.

IV. Coupled Cosserat Rod & Tendon Model

Having reviewed the classic Cosserat-rod model, the derivation a new model for tendon driven continuum manipulators in accordance with the various embodiments of the invention will now be presented. The derivation uses the Cosserat model of Section II to describe the elastic member and the classic Cosserat model for extensible strings to describe the tendons. For purposes of the model, the string and elastic structure models are coupled together by deriving the distributed loads that the tendons apply to the elastic structure in terms of the elastic structure's kinematic variables, and then incorporating these loads into the model.

A. Assumptions

Two standard assumptions are employed in the derivation. First, an assumption of frictionless interaction between the tendons and the channel through which they travel. This implies that the tension is constant along the length of the tendon. Frictional forces are expected to increase as the curvature of the robot increases due to larger normal forces, but the assumption of zero friction is valid if low friction materials are used, which is the case for the experimental prototype discussed below. Second, the locations of the tendons within the cross section of the robot are assumed not to change during the deformation. This assumption is valid for designs which use embedded sleeves or channels with tight tolerances, as well as designs which use closely spaced tendon guide portions.

B. Tendon Kinematics

One can separate the terms f and l in the equations in (5) into truly external distributed loads, $f_e$ and $l_e$, and distributed loads due to tendon tension, $f_t$ and $l_t$.

$$f = f_e + f_t$$

$$l = l_e + l_t. \qquad (7)$$

In order to derive $f_t$ and $l_t$, one starts by defining the path in which the tendon is routed along the robot length. Note that this path can be defined by channels or tubes within the elastic structure. The elastic structure can be a homogeneous elastic structure or a series of support disks on an elastic member—both of which afford considerable flexibility in choosing tendon routing. In the experimental prototype, many holes are drilled around the periphery of each support disk, allowing easy reconfiguration of tendon path as desired.

Figure 4:
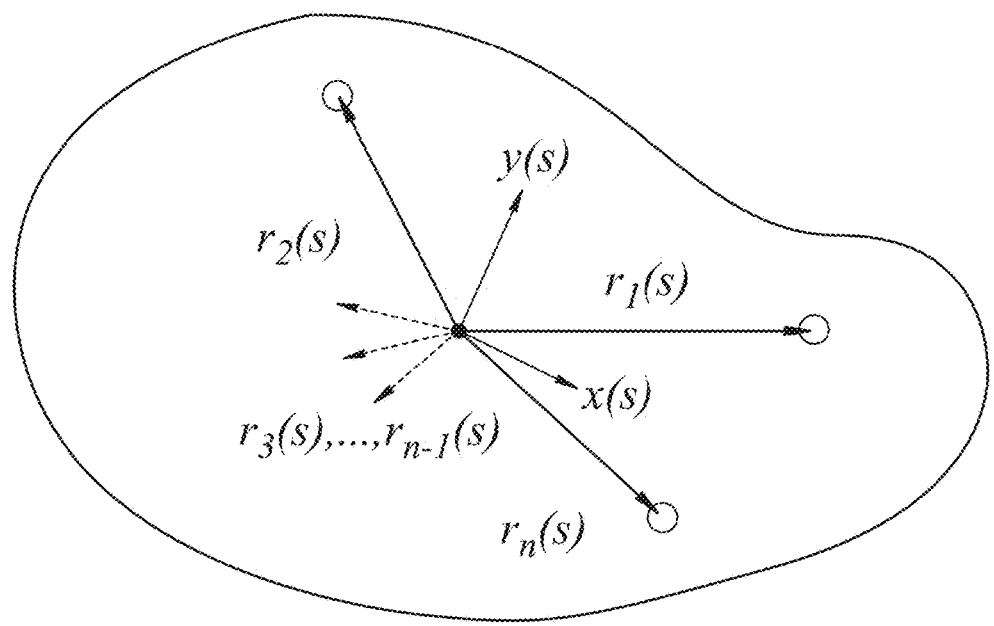
FIG. 4 is an illustration of a general cross section of the continuum robot material or support disk, showing tendon locations.
Figure 5:
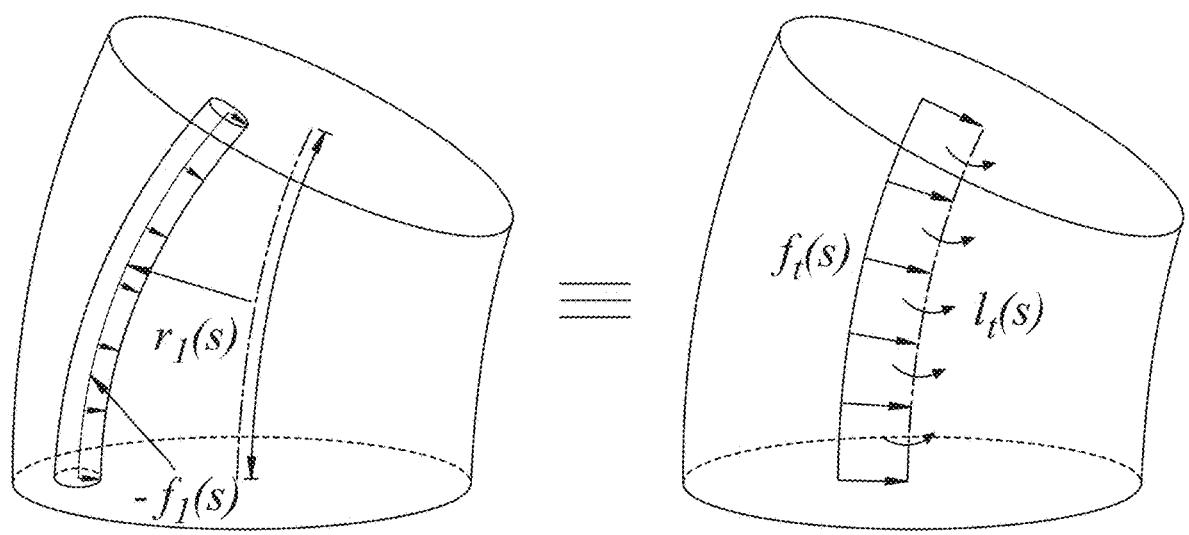
FIG. 5 is an illustration of a small section of a rod showing how the force distribution that the tendon applies to its surrounding medium is statically equivalent to a combination of force and moment distributions on the elastic member itself.

A convenient way to mathematically describe the tendon routing path is to define the tendon location within the robot cross section as a function of the reference parameter s. Thus, the routing path of the $i^{th}$ tendon is defined by two functions $x_i(s)$ and $y_i(s)$ that give the body-frame coordinates of the tendon as it crosses the x-y plane of the attached elastic structure frame at s. As shown in FIG. 4, a vector from the origin of the attached frame to the tendon location is then given in attached frame coordinates by $$r_i(s) = [x_i(s) y_i(s) 0]^T, \qquad (8)$$

The parametric space curve defining the tendon path in the global frame when the robot is in its undeformed reference configuration is then given by $$p_i^*(s) = R^*(s) r_i(s) + p^*(s).$$

Similarly, when the robot is deformed due to tendon tension or external loads, the new tendon space curve will be $$p_i(s) = R(s) r_i(s) + p(s). \qquad (9)$$

C. Distributed Forces on Tendons

The governing differential equations for an extensible string can be derived by taking the derivative of the static equilibrium conditions for a finite section. This results in the same equation for the internal force derivative as in equation (2).

$$\dot{n}_i(s) + f_i(s) = 0, \qquad (10)$$

where $f_i(s)$ is the distributed force applied to the $i^{th}$ tendon per unit of s, and $n_i(s)$ is the internal force in the tendon. In contrast to a Cosserat rod, an ideal string has the defining constitutive property of being perfectly flexible, meaning it cannot support internal moments or shear forces, but only tension which is denoted by $\tau_i$. This requires that the internal force be always tangent to the curve $p_i(s)$. Thus, one can write $$n_i(s) = \tau_i \frac{\dot{p}_i(s)}{\|\dot{p}_i(s)\|}. \qquad (11)$$

If friction were present, $\tau_i$ would vary with s, but under the frictionless assumption, it is constant along the length of the tendon. Using (10) and (11) one can derive the following expression for the distributed force on the tendon (see Appendix for Derivation):

$$f_i(s) = -\dot{n}_i = \tau_i \frac{\hat{\dot{p}}_i^2}{\|\dot{p}_i\|^2} \ddot{p}_i. \qquad (12)$$

D. Tendon Loads on Elastic Structure

One can now write the collective distributed loads $f_t$ and $l_t$ that the tendons apply to the elastic member, in terms of the individual forces on the tendons and their locations in the elastic structure cross-section (or in the case of guide discs, the cross-section of the elastic member supporting the discs). The total distributed force is equal and opposite to the sum of the individual force distributions on the tendons shown in equation (12), namely, $$f_t = -\sum_{i=1}^{n} f_i.$$

The distributed moment at the elastic member centroid is the sum of the cross products of each moment arm with each force. Thus, $$l_t = -\sum_{i=1}^{n} (p_i - p)^\wedge f_i = -\sum_{i=1}^{n} (R r_i)^\wedge f_i.$$

Substituting equation (12), yields $$f_t = -\sum_{i=1}^{n} \tau_i \frac{\hat{\dot{p}}_i^2}{\|\dot{p}_i\|^3} \ddot{p}_i, \qquad (13)$$

$$l_t = -\sum_{i=1}^{n} \tau_i (R r_i)^\wedge \frac{\hat{\dot{p}}_i^2}{\|\dot{p}_i\|^3} \ddot{p}_i.$$

One can then express these total force and moment distributions in terms of the kinematic variables u, v, R and p so that one can substitute them into equations (7) and (5). To do this, one expands $\dot{p}$ and $\ddot{p}$. Differentiating equation (9) twice yields, $$\dot{p} = R(\hat{u} r_i + \dot{r}_i + v),$$

$$\ddot{p} = R(\hat{u}(\hat{u} r_i + \dot{r}_i + v) + \dot{\hat{u}} r_i + \hat{u} \dot{r}_i + \ddot{r}_i + \dot{v}). \qquad (14)$$

It is noted that $\ddot{p}$ is a function of $\dot{u}$ and $\dot{v}$. Therefore, substituting these results into equation (13), and equation

(13) into the rod model equation (5) via equation (7), one can obtain an implicitly defined set of differential equations. Fortunately, the resulting equations are linear in u and v, and it is therefore possible to manipulate them into an explicit form. Rewriting them in this way (such that they are amenable to standard numerical methods) is the topic of the following subsection.

E. Explicit Decoupled Model Equations

The coupled elastic structure & tendon model is given in implicit form by equations (5), (7), (13), and (14). In this subsection, these implicit equations are manipulated into explicit, first-order, state-vector form. To express the result concisely, some intermediate matrix and vector quantities are defined, starting with equation (14) expressed in body-frame coordinates, i.e.

$$\dot{p}_i^b = \hat{u} r_i + \dot{r}_i + v,$$

$$\ddot{p}_i^b = \hat{u} \dot{p}_i^b + \dot{\hat{u}} r_i + \hat{u} \dot{r}_i + \ddot{r}_i + \dot{v}.$$

Now define Matrices $A_i$, A, $B_i$, and B, as well as vectors $a_i$, a, $b_i$, and b, as follows:

$$A_i = -r_i \frac{(\hat{p}_i^b)^2}{\|\dot{p}_i^b\|^3}, B_i = \hat{r}_i A_i$$

$$A = \sum_{i=1}^{n} A_i, B = \sum_{i=1}^{n} B_i,$$

$$a_i = A_i(\hat{u}\dot{p}_i^b + \hat{u}\dot{r}_i + \ddot{r}_i), b_i = \hat{r}_i a_i$$

$$a = \sum_{i=1}^{n} a_i, b = \sum_{i=1}^{n} b_i,$$

to find that $f_t$ and $l_t$ can now be expressed as $$f_t = R\left(a + A\dot{v} + \sum_{i=1}^{n} A_i \hat{u} r_i\right),$$ (15)

$$l_t = R\left(b + B\dot{v} + \sum_{i=1}^{n} B_i \hat{u} r_i\right).$$

The vector terms $\sum_{i=1}^{n} A_i \hat{u} r_i$ and $\sum_{i=1}^{n} B_i \hat{u} r_i$ are both linear in the elements of $\dot{u}$. Therefore, it is possible to express them both by equivalent linear operations on $\dot{u}$. That is, one can define matrices G and H as $$G = \sum_{i=1}^{n} [A_i \hat{e}_1 r_i \quad A_i \hat{e}_2 r_i \quad A_i \hat{e}_3 r_i]$$

$$H = \sum_{i=1}^{n} [B_i \hat{e}_1 r_i \quad B_i \hat{e}_2 r_i \quad B_i \hat{e}_3 r_i]$$

where $e_1$, $e_2$, and $e_3$ are the standard basis vectors [1 0 0], [0 1 0], and [0 0 1]. Then, equation (15) becomes $$f_t = R(a + A\dot{v} + G\dot{u}),$$

$$l_t = R(b + B\dot{v} + H\dot{u}),$$

Substituting tendon load expressions into the last two equations in (5) and rearranging them provides $$(D+A)\dot{v} + G\dot{u} = d$$

$$B\dot{v} + (C+H)\dot{u} = c$$

where the vectors c and d are functions of the state variables as shown below.

$$d = D\dot{v}^* - (\hat{u}D + \dot{D})(v - v^*) - R^T f_e - a$$

$$c = C\dot{u}^* - (\hat{u}C + \dot{C})(u - u^*) - \hat{v}D(v - v^*) - R^T l_e - b.$$

One can now easily write the governing equations as $$\dot{p} = Rv$$ (17)

$$\dot{R} = R\hat{u}$$

$$\begin{bmatrix} \dot{v} \\ \dot{u} \end{bmatrix} = \begin{bmatrix} D+A & G \\ B & C+H \end{bmatrix}^{-1} \begin{bmatrix} d \\ c \end{bmatrix}.$$

Noting that the quantities on the right hand side of equation (17) are merely functions of the state variables and system inputs (u, R, $\tau_n$, $f_e$ and $l_e$) one arrives at a system of differential equations in standard explicit form, describing the shape of a continuum robot with any number of generally routed tendons and with general external loads applied.

This system can be solved by any standard numerical integration routine for systems of the form $\dot{y}=f(s,y)$. The required matrix inverse may be calculated (either numerically or by obtaining a closed form inverse) at every integration step, or one could alternatively rewrite the equations as a system with a state dependent mass matrix on the left hand side and use any standard numerical method for solving $M(y,s)\dot{y}'=f(s,y)$. For purposes of the simulations and experiments in accordance with the various embodiments of the invention, numerically inversion is used.

F. Boundary Conditions

When tendon i terminates at $s=l_i$ along the length of the robot, it applies a point force to its attachment point equal and opposite to the internal force in the tendon given by equation (11). Thus, the point force vector is given by $$F_i = -n_i(\ell_i) = -\tau_i \frac{\dot{p}_i(\ell_i)}{\|\dot{p}_i(\ell_i)\|}.$$ (18)

With a moment arm of $p_i(l_i) - p(l_i)$, this force creates a point moment $L_i$ at the elastic member centroid of, $$L_i = -\tau_i (R(\ell_i) r_i(\ell_i))^\wedge \frac{\dot{p}_i(\ell_i)}{\|\dot{p}_i(\ell_i)\|}.$$ (19)

If at some location $s=\sigma$, point loads $F(\sigma)$ and $L(\sigma)$ (resulting from tendon terminations or external loads) are applied to the elastic structure, the internal force and moment change across the boundary $s=\sigma$ by, $$n(\sigma^-) = n(\sigma^+) + F(\sigma),$$

$$m(\sigma^-) = m(\sigma^+) + L(\sigma),$$ (20)

where $\sigma^-$ and $\sigma^+$ denote locations just before and just after $s=\sigma$. Any combination of external point loads and tendon termination loads can be accommodated in this way.

G. Point Moment Model

Figure 6:
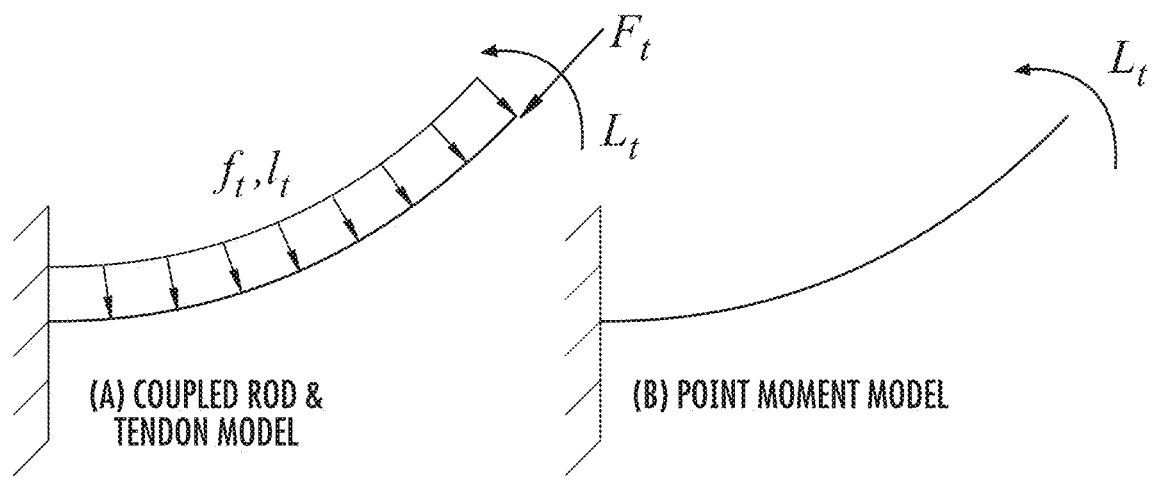
FIG. 6 is an illustration schematically showing (a) the coupled Cosserat rod and tendon approach that includes all of the tendon loads and (b) the point moment approach only includes the attachment moment.

In prior tendon robot models, tendon actuation has often been modeled by simply applying the pure point moment in equation (19) to an elastic structure model at the location where each tendon is attached, without considering the point force at the attachment point and the distributed tendon loads along the length (see FIG. 6). This approach is convenient because it allows one to use the classical Cosserat rod equations by simply applying boundary conditions that take into account the tendon termination moments.

This approximation for planar robots is justified since the effects of the point force and the distributed loads effectively "cancel" each other, leaving only the point moment. Thus, as shown in FIG. 1 this approach yields almost exactly the same final shape as the full coupled model when the robot deformation occurs in a plane.

However, as shown in FIG. 1, the two approaches diverge as the robot shape becomes increasingly non-planar due to a transverse load at the tip. In Section V, an investigation of the accuracy of both approaches a set of experiments on a prototype robot is provided.

V. Dynamic Model

Based on the coupled elastic structure and tendon model presented above for static continuum robot deformations, a model for the dynamics of a continuum robot with general tendon routing is derived. Such a model will be useful for analyzing the characteristics of specific designs as well as the development of control algorithms similar to those derived for planar robots with straight tendons. As shown below, adding the necessary dynamic terms and equations results in a hyperbolic system of partial differential equations, which can be expressed in the standard form $$y_t = f(s,t,y,y_s), \quad (21)$$

where a subscript s or t is used in this section to denote partial derivatives with respect to the reference parameter s and time t respectively.

Two new vector variables are introduced, q and ω, which are the body frame linear and angular velocity of the rod at s. These are analogous to u and v respectively, but are defined with respect to time instead of arc length. Thus, $$p_t = Rq \quad R_t = R\hat{\omega}. \quad (22)$$

Recalling from equations in (5) that $$p_s = Rv \quad R_s = R\hat{u}, \quad (23)$$

and using the fact that $p_{st} = p_{ts}$ and $R_{st} = R_{ts}$ one can derive the following compatibility equations, $$u_t = \omega_s + \hat{u}\omega \quad v_t = q_s + \hat{u}q - \hat{\omega}v, \quad (24)$$

Equations (2) and (3) describe the static equilibrium of the rod. To describe dynamics, one can add the time derivatives of the linear and angular momentum per unit length in place of the zero on the right hand side, such that they become, $$\dot{n} + f = \rho A p_{tt}, \quad (25)$$

$$\dot{m} + \dot{p} \times n + l = \partial_t(R\rho J\omega), \quad (26)$$

where ρ is the mass density of the elastic structure, A is the cross sectional area of the elastic structure, and J is the matrix of second area moments of the cross section. Expanding these and applying the equations in (24) one can obtain a complete system in the form of equation (21), $$p_t = Rq$$

$$R_t = R\hat{\omega}$$

(27)

-continued $$v_i = q_s + \hat{u}q - \hat{\omega}v$$

$$u_i = \omega_s + \hat{u}\omega$$

$$q_t = \frac{1}{\rho A}(D(v_s - v_s^*) + (\hat{u}D + D_s)(v - v^*) + R^T(f_c + f_t) - \rho A\hat{\omega}q)$$

$$\omega_t = (\rho J)^{-1}(C(u_s - u_s^*) +$$

$$(\hat{u}C + C_s)(u - u^*) + \hat{v}D(v - v^*) + R^T(l_s + l_t) - \hat{\omega}\rho J\omega)$$

where $f_t$ and $l_t$ can be computed using the equations in (16). Typically, conditions at t=0 are given for all variables along the length of the robot, and the boundary conditions of Subsection IMF apply for all times.

A. Dynamic Simulation

To illustrate the capability of the equations in (27) to describe the time evolution of the shape of a continuum robot with general tendon routing, the following dynamic simulation of a robot whose elastic structure is identical to that of the experimental prototype described below is provided. The robot contains a single tendon routed in a helical where the tendon makes one complete revolution around the shaft as it passes from the base to the tip. This routing path is the same as the one for tendon 5 in the prototype, which is specified in Table 1.

TABLE I

TENDON ROUTING PATHS USED IN EXPERIMENTS

| Tendon (i) | 1 | 2 | 3 | 4 | 5 | 6 |
|---|---|---|---|---|---|---|
| $x_i(s)$ (mm) | 8 | 0 | −8 | 0 | 8cos(2πs/l) | refer to (28) |
| $y_i(s)$ (mm) | 0 | 8 | 0 | −8 | 8sin(2πs/l) | refer to (28) |

Figure 7:
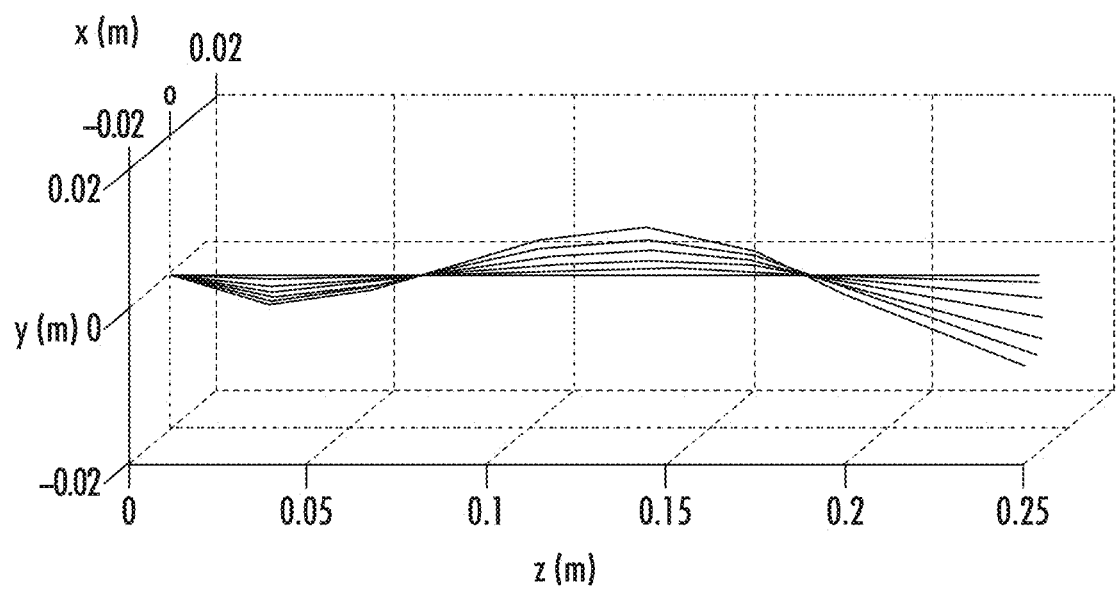
FIG. 7 is an x-y-z plot of the time response of a Continuum robot with a helical tendon is simulated for a step input in tendon tension.

FIG. 7 shows snapshots of the robot backbone shape at millisecond intervals after a step input of 5 Newtons of tendon tension was applied. For the numerical simulation Richtmyer's two-step variant of the Lax-Wendroff finite-difference scheme was implemented.

The maximum length of the time step for any explicit time-marching algorithm for hyperbolic partial differential equations is limited by the Courant-Friedriechs-Lewy condition for stability. This is a fairly restrictive condition for dynamic rod problems because the shear, extension, and torsional vibrations are so fast that a very small is required in order to capture them without the simulation becoming unstable. An active research field in mechanics and computer graphics simulation is to find reduced—order models of elastic structures that are physically accurate and yet capable of being simulated in real-time. This simulation confirms the intuition that the elastic structure should move towards a helical very when the helical tendon undergoes a step in tension.

VI. Experimental Validation

Figure 8:
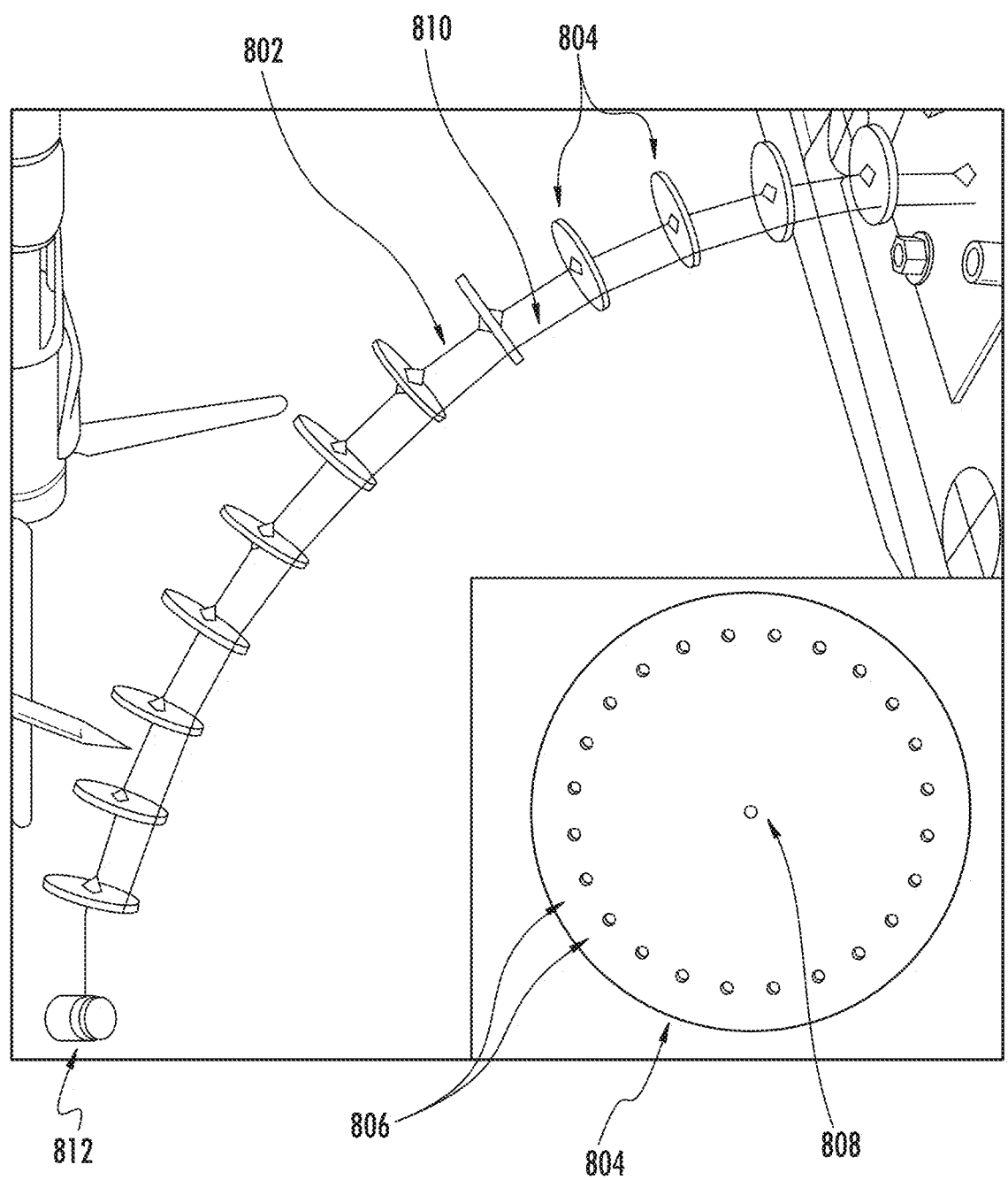
FIG. 8 is shows an exemplary continuum robot configured to operate in accordance with the various embodiments, where the inset shows a detailed view of the tendon guide portions.

Below are described several different experiments conducted using a continuum robot prototype with a variety of tendon paths and external loading conditions applied A. Prototype Constructions A prototype robot in accordance with the various embodiments is shown in FIG. 8. The elastic structure consists of a central elastic member 802 is a spring steel rod (ASTM A228) of length l=242 mm and diameter d=0.8 mm with tendon guide portions 804 consisting of 12 stand-off disks, 20 mm in diameter, spaced 20 mm apart along its length. The disks were laser cut from 1.57 um thick PTFE filled Delrin plastic to minimize friction with the tendons. As shown in the inset of FIG. 8, 24 small pass-through holes 806 were laser cut in a circular pattern at a radius of 8 mm from the center of each disk. The elastic member rod 802 was passed through the center holes 808 of the disks and each was fixed to it using Loctite 401. For tendons 810, 0.36 mm PTFE coated fiberglass thread were used. Each tendon 810 was run through various pass-through holes along the robot and knotted at the end, after passing through the final support disk. The optimal ratio of tendon support spacing to offset distance from the elastic member was found to be 0.4, and the prototype was designed to exactly match this ratio.

Although the exemplary robot configuration utilizes standoff disks to provide the tendon guide portions, the various embodiments are not limited in this regard. Rather, any of means of coupling the tendons to the elastic member to cause deformation of the elastic member can be used in the various embodiments. Further, a particular combination of materials, spacing of guide portions, and openings in the guide portions is provided, the various embodiments are not limited in this regard. Rather, any variations on the combination recited above can be used with the various embodiments. Additionally, the methods above can be used with any number of tendons. In such embodiments, the tendons can extend along a same portion of the length of the elastic member or the tendons can extend over different portions of the length of the elastic member, including overlapping portions.

The tendon routing paths can be reconfigured on this robot by "re-threading" the tendons through a different set of holes in the various support disks. The robot's self-weight distribution was measured to be 0.47 N/m, which is enough to cause significant deformation, producing 44 mm of downward deflection at the tip (18% of the total arc length) for zero tendon tension. This weight was incorporated into all model calculations as a distributed force.

B. Experimental Procedure

In each of the following experiments, known tensions were applied to tendons behind the base of the robot by passing the tendons over approximately frictionless pulleys and attaching them to hanging calibration weights. In those cases with applied point loads, weights 812 were also hung from the tip of the robot, as shown in FIG. 8.

In each experiment, a set of 3D elastic member points was collected by manually touching the elastic member with the tip of an optically tracked stylus as shown in FIG. 8. A MicronTracker 2 H3-60 (Claron Technology, Inc.) was used to track the stylus, which has a specified fiducial measurement accuracy of 0.20 mm.

C. Calibration

The base frame position of the robot can be determined accurately using the optically tracked stylus. The angular orientation of the robot elastic member as it leaves the base support plate is more challenging to measure (Note that the elastic member cannot be assumed to exit exactly normal to the plate due to the tolerance between the elastic member and the hole drilled in the plate, and a 2° angular error in base frame corresponds to an approximately 8 mm tip error when the robot is straight). Also, the effective stiffness of the elastic member was increased due to the constraints of the standoff disks and Loctite adhesive at regular intervals. To account for these uncertainties the effective Young's modulus and the set of XYZ Euler angles ($\alpha$, B, and $\gamma$) describing the orientation of the base frame were calibrated.

The calibration process was accomplished by sorting a preconstrained nonlinear optimization problem to find the set of parameters which minimizes the sum of the positional errors at the tip of the device for the set of 25 experiments with straight tendon paths described in Sec. V-D and Table II.

TABLE II

EXPERIMENTAL TENSIONS AND TIP LOADS

Experimental with Tendons 1-4 (Straight)

| Tension (N) | 0 | 0.98 | 1.96 | 2.94 | 2.94 | 2.94 | 4.91 |
|---|---|---|---|---|---|---|---|
| Tip Load (N) | 0 | 0 | 0 | 0 | 0.098 | 0.196 | 0 |

Experiments with Tendon 5 (Helical)

| Tension (N) | 0.98 | 1.96 | 2.94 | 4.91 | 4.91 | 4.91 | 6.87 |
|---|---|---|---|---|---|---|---|
| Tip Load (N) | 0 | 0 | 0 | 0 | 0.098 | 0.196 | 0 |

Experiments with Tendon 6 (Polynomial)

| Tension (N) | 1.50 | 2.46 | 3.66 | 4.91 | 4.91 |
|---|---|---|---|---|---|
| Tip Load (N) | 0 | 0 | 0 | 0 | 0.0196 |

In other words, for the parameter set P={E, $\alpha$, B, $\gamma$}:

$$P_{cal} = \underset{P}{\mathrm{argmin}}\left(\sum_{i=1}^{25} e_k\right)$$

where $e_k = \|p_{model}(\ell) - p_{date}(\ell)\|_k$ is the Euclidean distance between the model tip prediction and the data in experiment k. To implement this minimization, the Nelder-Meade simplex algorithm was used.

To ensure fair comparison of the coupled model and the point moment model, the calibration procedure was performed separately for each model. Results are shown in Table III.

TABLE III

NOMINAL AND CALIBRATED PARAMETERS

| Parameter | Nominal Value | Calibrated Value (Point Moment Model) | Calibrated Value (Coupled Model) |
|---|---|---|---|
| E (GPa) | 210 | 227.9 | 229.6 |
| $\alpha$ (deg) | 180 | 177.7 | 177.9 |
| $\beta$ (deg) | 0 | 2.2 | 2.2 |
| $\gamma$ (deg) | −90 | −89.6 | −89.7 |

Note that the similarity in calibrated Euler angles and their low deviation from nominal provides confidence that the correct base frame was obtained for both models. It is also important to note that the models contain the same number of parameters, so a fair comparison can he made, As expected, the calibrated values for Young's modulus are higher than the nominal value of 210 GPa for spring steel, due to the increased stiffness provided by the disks and glue. Poisson's ratio was held constant at v=0.3125 during calibration so that the shear modulus was correctly scaled relative to Young's modulus.

D. Straight Tendon Results and Model Comparison

Table I details the location of the tendon routing paths used in the experiments in terms of $x_i(s)$ and $y_i(s)$ as defined in (8). Twenty-five (25) experiments were performed (detailed in Table II) with straight tendon paths in order to compare the accuracy of the new coupled model with that of the point moment model. The tip error statistics for both models with calibrated parameters is detailed in Table IV.

TABLE IV

MODEL TIP ERRORS FOR STRAIGHT TENDON EXPERIMENTS

| Tip Error Statistic (mm) | mean | std. dev. | min | max |
|---|---|---|---|---|
| 13 Cases with In-Plane Loads | | | | |
| Point Moment Model | 3.5 | 1.4 | 1.2 | 5.6 |
| Coupled Model | 3.1 | 1.3 | 0.3 | 5.3 |
| 12 Cases with Out-of-Plane Loads | | | | |
| Point Moment Model | 9.8 | 5.5 | 1.7 | 16.2 |
| Coupled Model | 4.1 | 2.1 | 0.6 | 7.9 |

Figure 9:
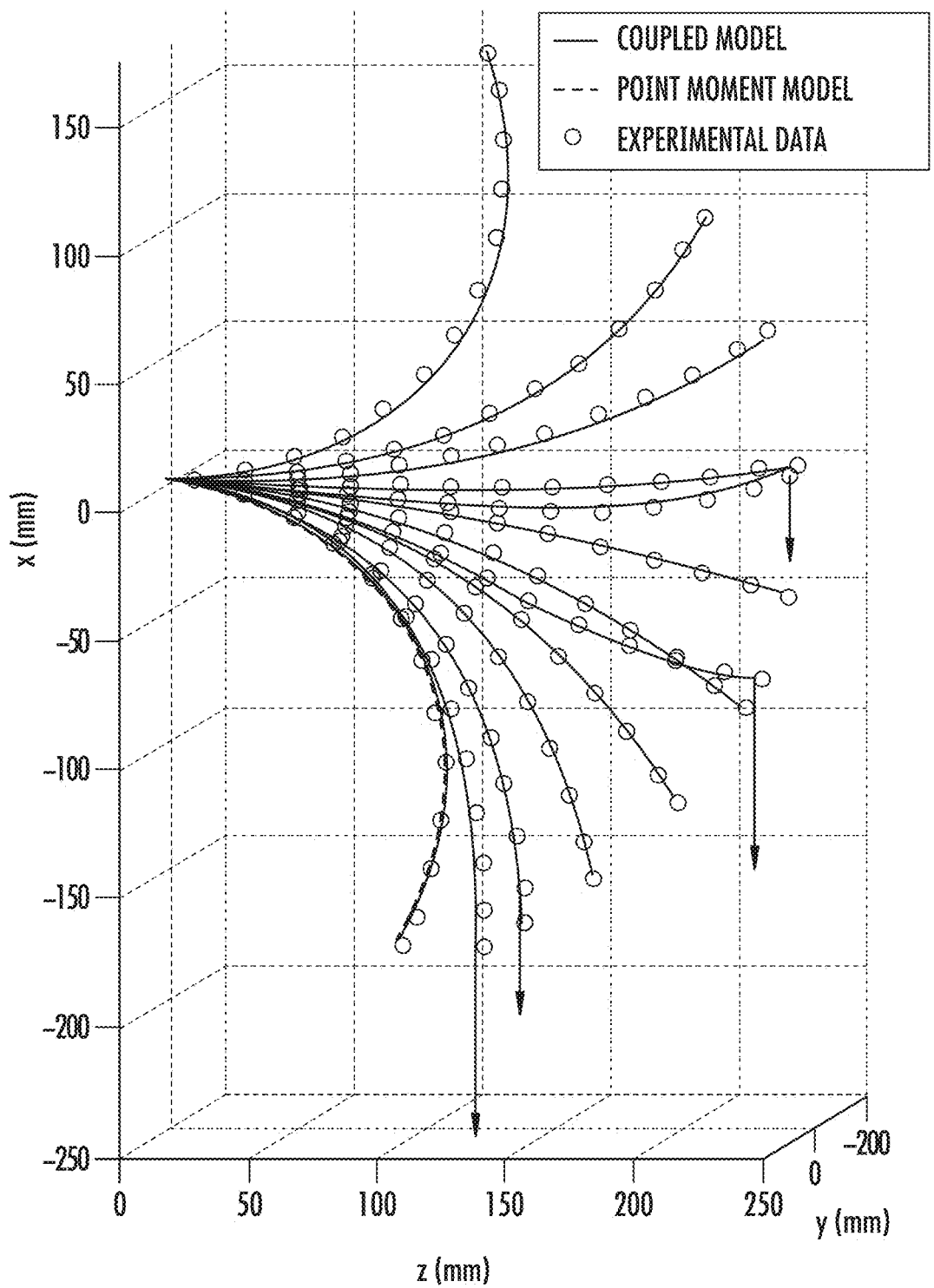
FIG. 9 is an x-y-z plot of the actual and simulated result of in-plane loading of an exemplary continuum robot using a straight tendon.
Figure 10A:
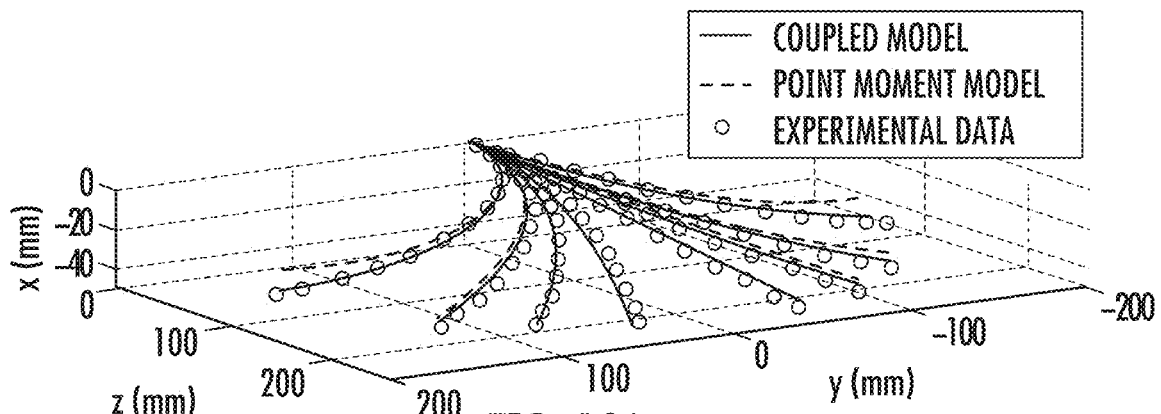
FIG. 10 is an x-y-z plot of the actual and simulated result of out-of-plane loading of an exemplary continuum robot using a straight tendon.
Figure 10B:
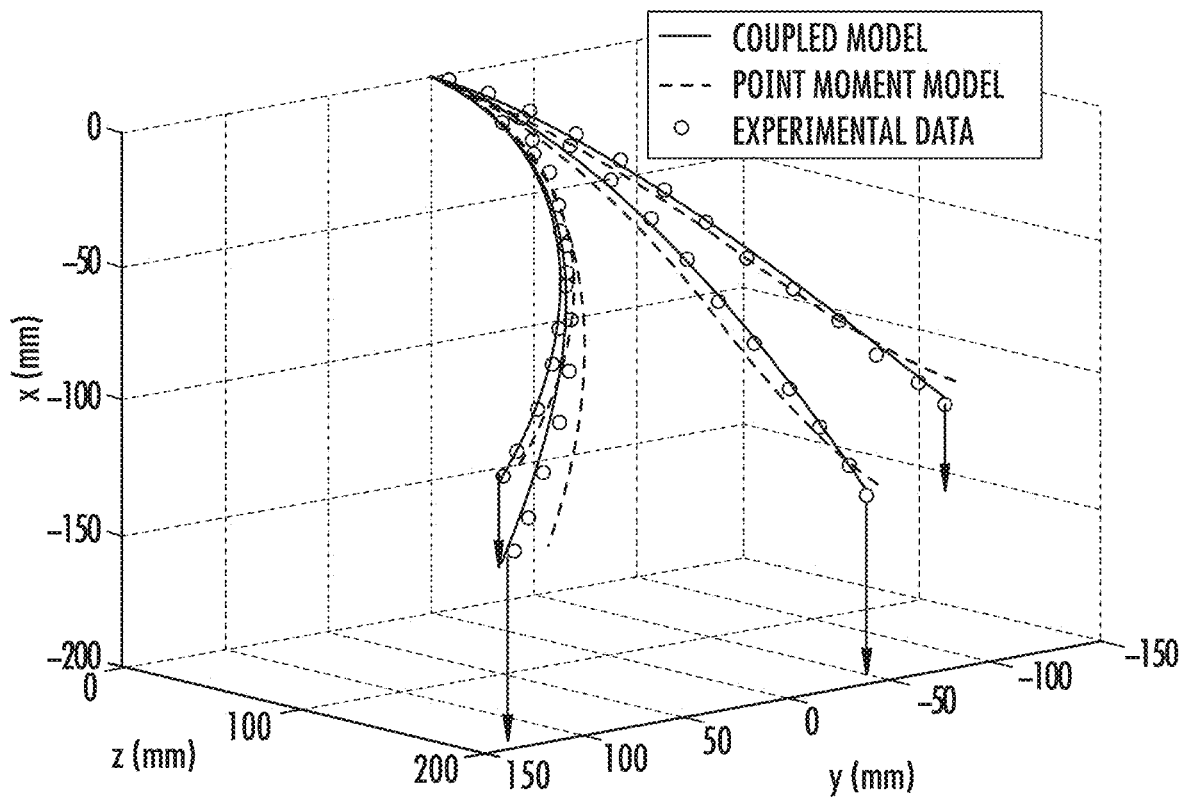

The results for in-plane loading are accurate for both models, as shown in FIG. 9. FIG. 9 is an x-y-z plot of the actual and simulated result of in-plane loading of an exemplary continuum robot using a straight tendon. Shown in FIG. 9 are the 13 experimental cases with in-plane external loads. The tendons on the top and bottom of the robot (tendons 1 and 3) were tensioned and vertical tip loads were applied in four of the cases. Distributed gravitational loading is present in every case. As detailed in Table IV, both the coupled model and the point moment model are accurate and nearly identical for in-plane loads. In contrast, for out-of-plane loads, the coupled model provides more accurate predictions, as shown in FIG. 10. FIG. 10 is an x-y-z plot of the actual and simulated result of out-of-plane loading of an exemplary continuum robot using a straight tendon. Pictured in FIG. 10 are the twelve experimental cases with out-of-plane external loads. The tendons on the left and right of the robot (tendons 2 and 4) were tensioned. (a) Distributed loading (robot self-weight) applied, (b) additional tip loads applied. As detailed in Table IV, the data agrees with the coupled model prediction, but the point moment model becomes inaccurate as the out-of-plane load increases, and as the curvature increases.

With calibrated parameters, the mean tip error over all 25 straight tendon experiments was 3.6 mm for the coupled model. This corresponds to 1.5% of the total arc length of the robot. Note that experimental data points lie close to the model prediction along the entire robot length, and the error increases gradually along the robot length, so that tip error normalized by the robot length is a reasonable metric for the accuracy of the model.

E. A High-Tension, Large-Load, Straight Tendon Experiment

Figure 11:
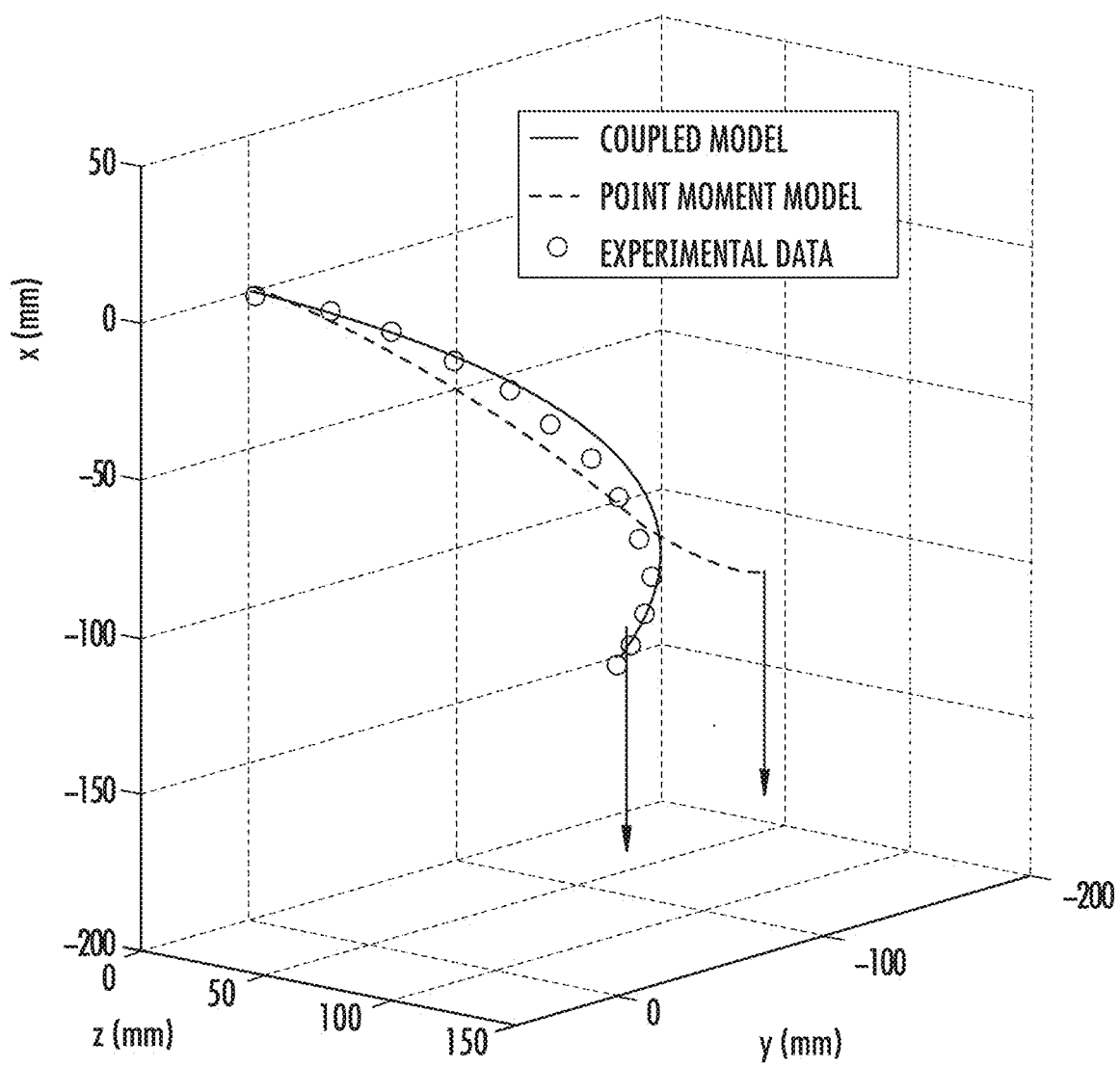
FIG. 11 is an x-y-z plot of the actual and simulated result of out-of-plane loading for an exemplary continuum robot using a straight tendon and high tension.

Also performed was one additional straight tendon experiment to see how the two approaches compare for a case of large tension and large out-of-plane load, similar to the case which is simulated in FIG. 1. Tendon 4 was tensioned to 6.38 N and a downward tip force of 0.196 N was applied. The resulting data and model predictions are shown in FIG. 11. FIG. 11 is an x-y-z plot of the actual and simulated result of out-of-plane loading for an exemplary continuum robot using a straight tendon and high tension. As illustrated in FIG. 11, the two models produce very different results. FIG. 11 shows that the coupled model prediction lies much closer to the data. Here, the tip error of the point moment model is 57 mm (23.5% of robot length), while the coupled model tip error is 12.8 mm (5.3% of robot length).

F. Experiments with Helical Tendon Routing

Figure 12A:
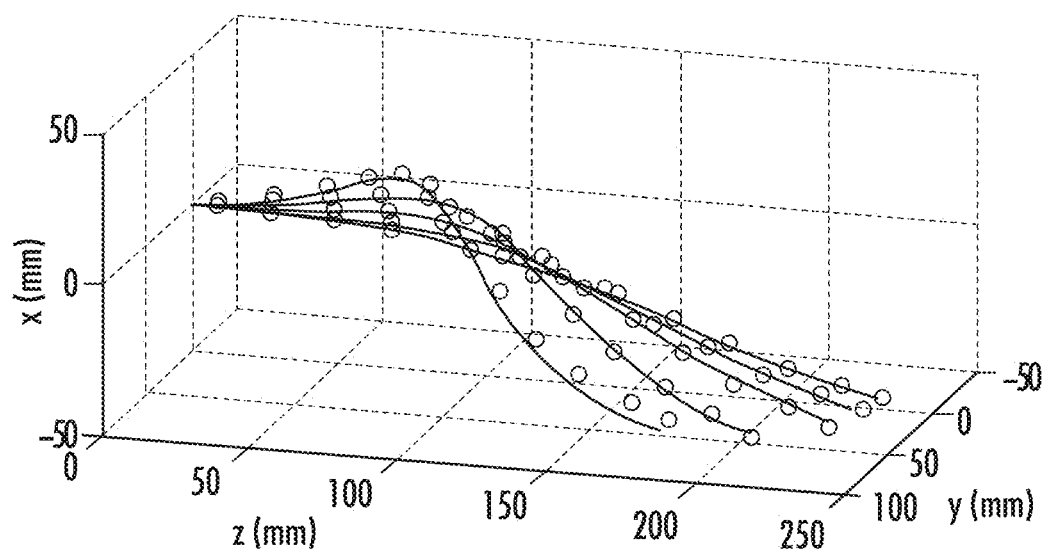
FIG. 12A is an x-y-z plot of the actual and simulated results of operation of an exemplary continuum robot using a helical tendon without a load.
Figure 12B:
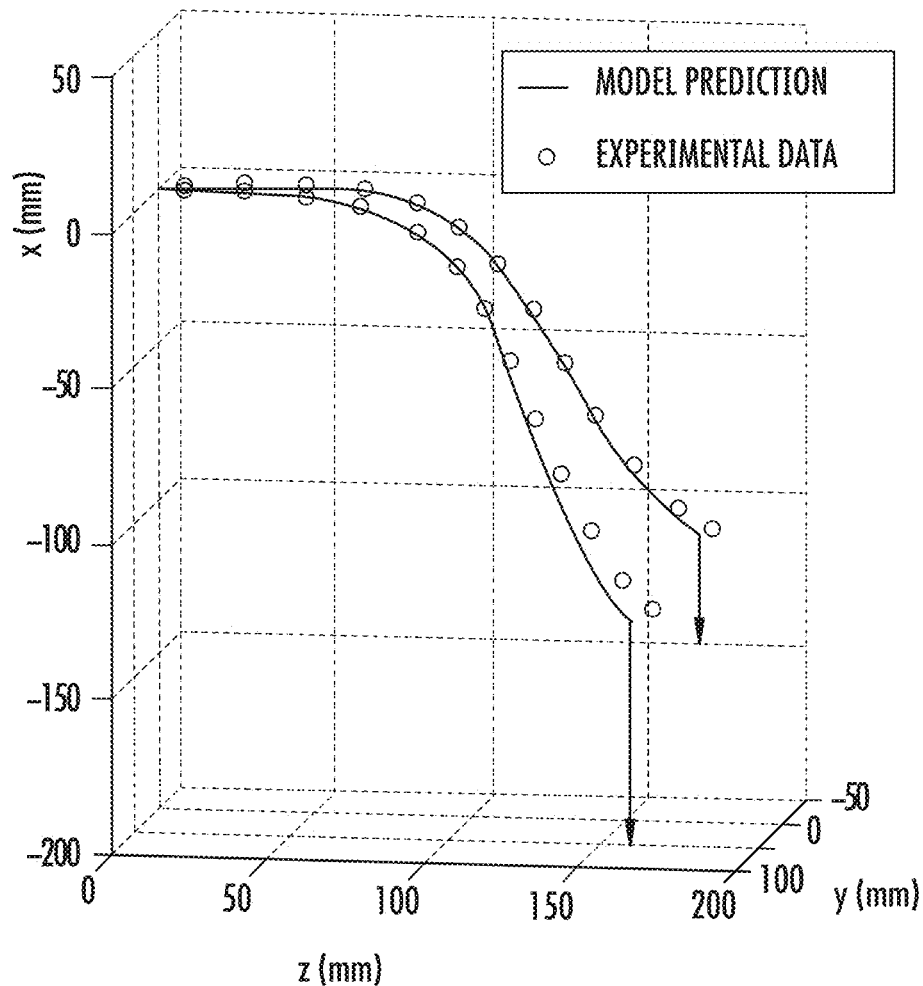
FIG. 12B is an x-y-z plot of the actual and simulated results of operation of an exemplary continuum robot using a helical tendon with a tip load.

To explore more complex tendon routing, helical routing paths were also evaluated. As given in Table I, the helical routing path winds through one complete revolution as it traverses the robot from base to tip. The tensions and tip loads for these experiments are detailed in Table II. Using the parameters calibrated from the previous straight tendon dataset, the resulting data and model predictions are plotted in FIGS. 12A and 12B. FIG. 12A is an x-y-z plot of the actual and simulated results of operation of an exemplary continuum robot using a helical tendon without a load. FIG. 12B is an x-y-z plot of the actual and simulated results of operation of an exemplary continuum robot using a helical tendon with a tip load. As seen from Table V, the model agrees with the data with a mean tip error of 5.5 mm. The small increase in error over the straight tendon cases may be due to increased frictional forces since the tension for the helical cases was higher.

TABLE V

COUPLED MODEL TIP ERRORS FOR NON-STRAIGHT TENDON EXPERIMENTS

| | mean | std. dev. | min | max |
|---|---|---|---|---|
| Tendon 5 (Helical) | 5.5 | 2.7 | 1.9 | 10.0 |
| Tendon 6 (Polynomial) | 4.6 | 1.9 | 2.7 | 7.2 |

G. Experiments with Polynomial Tendon Routing

Figure 13:
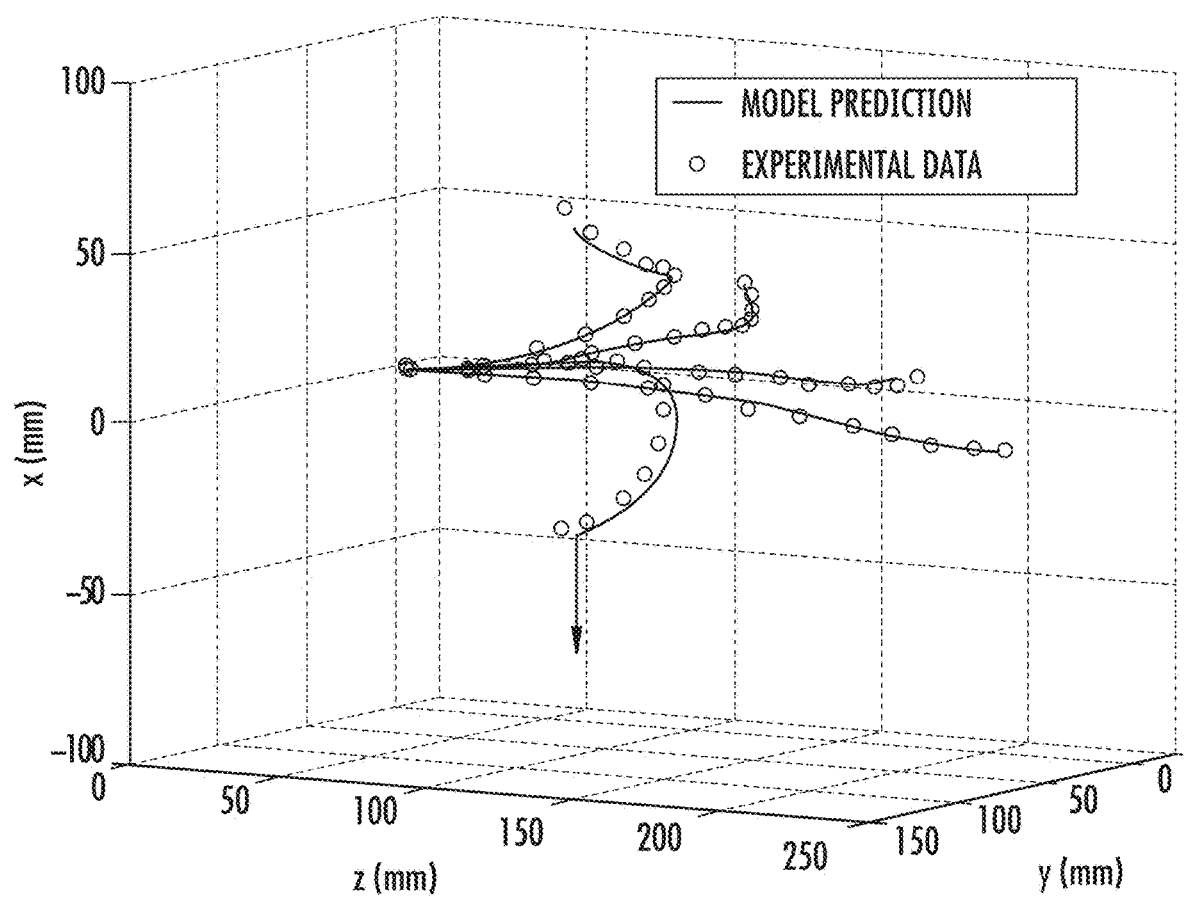
FIG. 13 is an x-y-z plot of the actual and simulated results of operation of an exemplary continuum robot using a polynomial tendon with tip loads according to Table II.

In order to further illustrate the model's generality, an additional experiment with a general curved tendon routing choice was performed. In particular, the routing path variables were parameterized by two trigonometric functions whose arguments are defined by a polynomial function of degree 4 as follows:

$$x_6(s) = 8 \cos(5887s^4 - 2849s^3 + 320s^2 + 6s)$$

$$y_6(s) = 8 \sin(5887s^4 - 2849s^3 + 320s^2 + 6s), \quad (28)$$

where s is in meters and $x_6$ and $y_6$ are in millimeters. This routing path starts at the top of the robot, wraps around to the right side for most of the length, and then returns to the top at the end of the robot. The tensions and loads are given in Table II, and the results are detailed in Table V and illustrated in FIG. 13. FIG. 13 is an x-y-z plot of the actual and simulated results of operation of an exemplary continuum robot using a polynomial tendon with tip loads according to Table II. The coupled model's predictions agree with the data, with a mean tip error of 4.6 mm. This set of experiments confirms the coupled model's ability to handle an arbitrary tendon routing choices.

H. Sources of Error

The largest source of measurement is likely the procedure of manually placing the tip of the on the robot during data capture. It is estimated that this uncertainty is at most 2 mm. In general, the largest model errors occurred when the tendons were under the greatest tension. This agrees with the intuition that effects of static friction should become more significant as the tension and curvature increase, However, the low overall errors suggest that neglecting static friction is justifiable for this prototype.

VII. System Configuration

Figure 14:
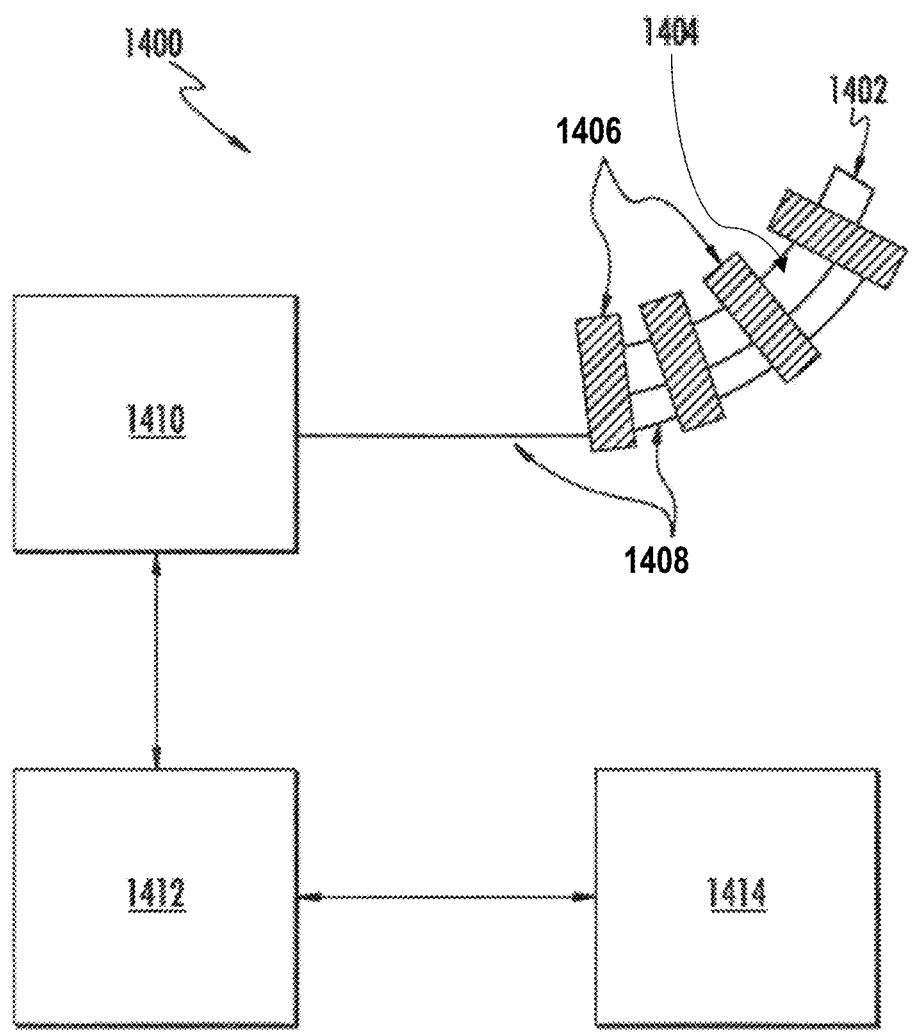
FIG. 14 is a schematic illustration of a continuum robot system 1400 in accordance with the various embodiments.

Accordingly, in the view of the foregoing, the equations above can be integrated into a continuum robot system, as shown in FIG. 14. FIG. 14 is a schematic illustration of a continuum robot system 1400 in accordance with the various embodiments. The system 1400 can include a continuum robot 1402 similar to that illustrated in FIG. 8. That is, the continuum robot 1402 can include an elastic member or backbone 1404 having one end or portion coupled to a support or base (not shown), a number of guide portions 1406, and at least one tendon 1408 extending through the guide portions and defining a tendon path, as described above. The system 1402 can further include an actuator/sensor 1410 for applying a force or tension and for ascertaining a current tension on the tendon 1408 to the tendon 1408. The system 1400 can also include a control system 1412 for operating the system 1400, which can include a computing device.

The system can have at least two modes of operation. In a first mode of operation, the actuator/sensor 1410 can generate signals indicative of a current tension on the tendon 1408. This signal can be recited by the control system 1412. The control system 1412 can then use the equations described above, particularly the governing equations at (17), to estimate a current or resulting shape of the member 1404. In particular, the governing equations at (17) can be solved to extract the shape of the member 1404. Additional sensors 1414, such as video sensors, can also be coupled to the control system 1412 to allow verification of this estimated shape. In a second mode of operation, the control system 1412 can also use the equations described above, particularly the governing equations at (17), to determine an amount of tension required for the member 1404 to achieve a desired shape. Thereafter, the control system 1412 can cause the actuator/sensor 1410 to adjust the tension on the tendon 1408. The additional sensors 141 can then be used to verify that the target shape has been achieved.

Using these two modes of operation, it is then possible to control the robot 1402 to perform various types of tasks, as the equations above allow one to detect and adjust the configuration of the robot 1402 in real-time based on measurement and adjustment of the tension of the tendon 1408. That is, a robot with increased dexterity can be provided. Such a robot can be useful for various applications. In particular, such robots would be useful for carry out procedures in confined spaces, as the increased dexterity would allow the user to maneuver the tip around obstructions in such spaces. For example, such robots could be used to reduce the invasiveness of some existing surgical procedures which currently cannot be performed using conventional robotic tools. Such procedures in transnasal skull base surgery, lung interventions, cochlear implantation procedures, to name a few. However, the various embodiments are not limited in this regard and the various methods and systems described herein can be used for any other procedure in which increased dexterity of the robot is desired or required.

VII. Alternate Embodiments with Rod-Type Actuators

Accordingly, in the view of the foregoing, the equations above can be integrated into a continuum robot system, as shown in FIG. 14. FIG. 14 is a schematic illustration of a continuum robot system 1400 in accordance with the various embodiments. The system 1400 can include a continuum robot 1402 similar to that illustrated in FIG. 8. That is, the continuum robot 1402 can include an elastic member or backbone 1404 having one end or portion coupled to a support or base (not shown), a number of guide portions 1406, and at least one tendon 1408 extending through the guide portions and defining a tendon path, as described above. The system 1402 can further include an actuator/sensor 1410 for applying a force or tension and for ascertaining a current tension on the tendon 1408. The system 1400 can also include a control system 1412 for operating the system 1400, which can include a computing device.

VII. Pre-Curved Rods

In some configurations, a pre-curved rod can be utilized. As used herein, the term "pre-curved rod" refers to a rod that changes direction in two- or three-dimensional space at least once (i.e., non-linear or have at least one bend or change in direction in space) in the absence of an external force. Thus, in the absence of any external forces being applied to a pre-curved rod, the pre-curved rod is configured to revert to its shape with changes in direction.

Pre-curved rods are useful for providing extended capabilities to a wide variety of surgical tools, including, but not limited to standard endoscopes, robotic endoscopes, continuum robots. The extended capabilities include: (1) enabling such devices to reach around "tighter corners" (i.e., achieve higher curvatures), (2) achieve larger workspaces, and (3) achieve novel motions (e.g., spinning the tip in place without moving the tip's position). Given these properties, the various embodiments of the invention can be used for a wide variety of surgical applications throughout the body. One example is retroflexed endoscopy, in which the endoscope enters a lumen or cavity and must turn through an angle between 90 and 360 degrees to operate "backwards", i.e., in a retroflexed manner, which is useful for both identifying and surgically removing polyps hidden by intestinal edges. Another example is Peroral Endoscopic Myotomy in which the endoscope must enter the stomach and then operate on the muscle of the sphincter through which the endoscope entered the stomach cavity.

Another advantage of pre-curved rods is that they provide greater dexterity in retroflexed configurations. Often, in a given procedure, an instrument may be capable of reaching a particular anatomical target, but just barely (i.e. the location is at the edge of the mechanism's workspace). This makes it very difficult for the surgeon to dexterously and effectively control the tip of the device. It is why retroflexed endoscopy, ERCP, and POEM are possible for expert surgeons, but highly challenging, and beyond the capabilities of all but the best surgeons. With the pre-curved strip-actuated design, the overall workspace of the mechanism can be greater (with or without precurvature), and thus sites that previously lay near the edge of the workspace are now comfortably within the workspace, resulting in easier control and increased dexterity of the tip around those previously difficult-to-reach locations.

In one embodiment of the invention, a device with pre-curved rods can be configured similar to that shown in FIG. 8. As previously discussed, an elastic structure can be provided and can be configured for holding guide discs at a desired spacing between discs. The rods can then be used to push and pull on one or more discs of the device, causing the overall shape to change. Each rod is affixed to one disc and is free to slide within pass-through holes in other discs of the device.

Figure 15:
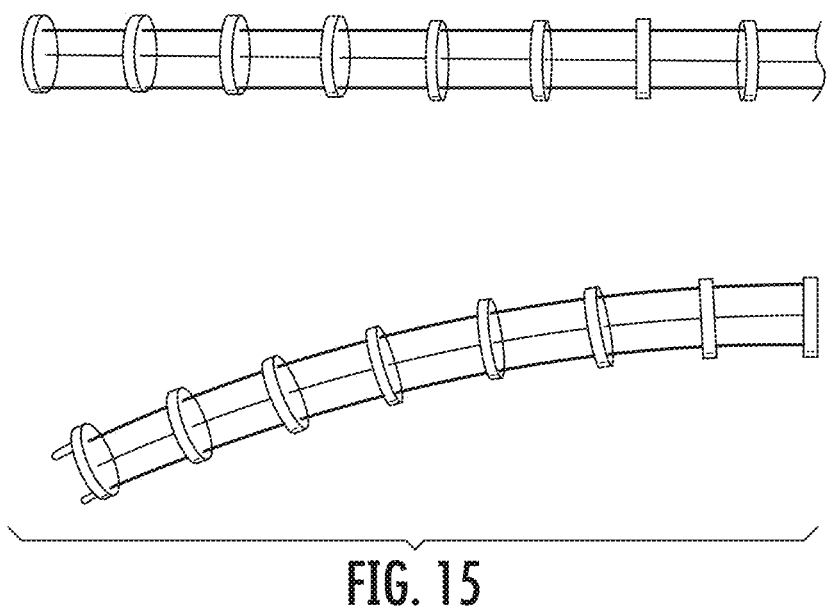
FIG. 15 is a photograph illustrating a continuum robot with straight rods (top) and a continuum robot with pre-curved rods (bottom) in accordance with the various embodiments.

As noted above, the rods can be pre-curved. For example, pre-curved, superelastic nitinol wires can be used. Thus the resulting shape of the device as a whole can be, for example, a circular arc when no forces are applied to the rods (i.e., when the device is in its "home" or undeflected position). FIG. 15 shows a straight rod device (top) and a pre-curved rod device (bottom) in the home position.

It should be noted that the home position of devices in accordance with the various embodiments is not limited solely to a circular arc configuration. Rather, the home position can be can any shape in three dimensional space. Thus, in a home position, a device in accordance with the various embodiments can include any number of bends and such bends can be circular and non-circular. In certain embodiments, the rod is not pre-curved and can be configured to have a low stiffness relative to the rods so as to conform to the home position of the rods, allowing the rod to sustain higher curvature changes than the rods.

In some embodiments, a rod can be configured have two degrees of freedom: (1) translated in/out (i.e., provide push/pull with respect to a disc) and (2) a rod can be rotated about its axis. Flexible surgical devices using straight wires or rods do not typically include a rotation feature. In particular, since rotation of a straight wire or rod would not result in a change in shape of the device, rotation would have no effect and thus, no use. In contrast, in the case of a pre-curved rod, the rotation of the rod alone can be utilized to change the shape of the device. Therefore, in the various embodiments, different combinations of rotation and translation for each pre-curved rod can permit a device with pre-curved rods in accordance with the various embodiments to produce shapes that would not be possible with straight rods or tendons. For example, non-circular curves. A mechanics-based model of the device, described in greater detail below, can then be utilized in selecting amounts of push/pull and rotation to produce a desired shape of the device.

Figure 16A:
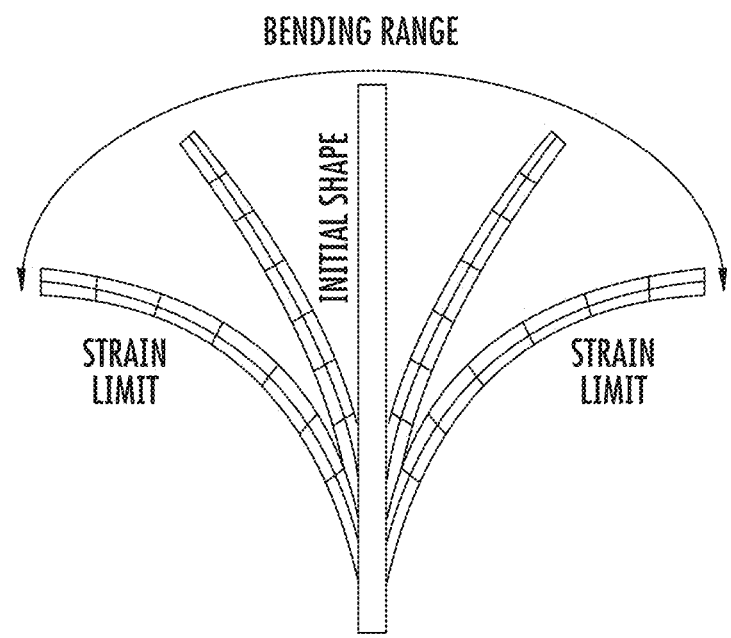
FIG. 16A illustrates the range of motion permitted for continuum robots using straight rods in accordance with the various embodiments.
Figure 16B:
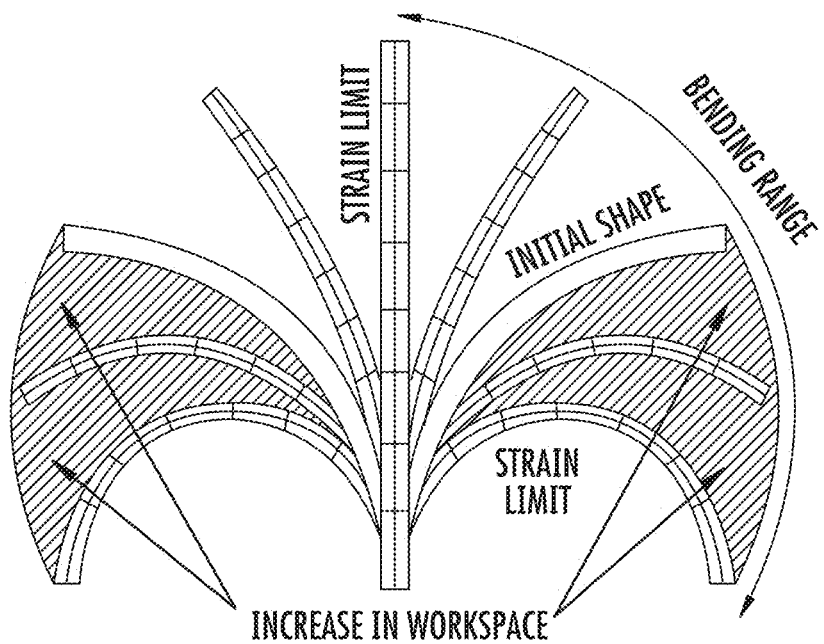
FIG. 16B illustrates the range of motion permitted for continuum robots using pre-curved rods in accordance with the various embodiments.

One particular useful shape permitted by a device including pre-curved rods in accordance with the various embodiments is a circular arc with high curvature, which can be obtained by pushing the rods on the outside of the curve and pulling those on the inside of the curve. These tighter possible curvatures result in a greater workspace when compared to the tendon configuration. In a tendon configuration, as shown in FIG. 16A, curvature is limited on either side at the point where the strain limit of one of the rods is reached. In the pre-curved wire case, the workspace is "biased" so that the strain limit is reached near a straight configuration on one side and at a very tight curvature on the other, as shown in FIG. 16B. Rotation is used to provide such biasing and therefore enables the device to reach this maximum curvature in any direction. Another interesting feature is that it is possible to rotate the tip of the tool in place without rotating the entire device.
This type of motion is accomplished by rotating the rods and the elastic structure in an equal and opposite fashion, so that shape is maintained in space while the tip of the tool rotates with the elastic structure.

As discussed above, devices with pre-curved rods in accordance with the various embodiments can be characterized and controlled using a mechanics-based mathematical model which can be used to predict the device's shape as a function of rod translation, rotation, and pre-curvatures as well as the geometric and material properties of the device. The model parameterizes the shape of the device by assuming that the corresponding elastic structure (e.g., an elastic support member and discs) is composed of multiple helical segments (one between each pair of spacing discs), where the shape of each helical segment is defined by the amount of bending and torsion within the elastic structure. The shape of the rods in the device can then be determined by the shape of the elastic structure and the locations of the pass-through holes relative to the elastic structure. The model also allows for the rods to twist axially within the pass-through holes.

Figure 17:
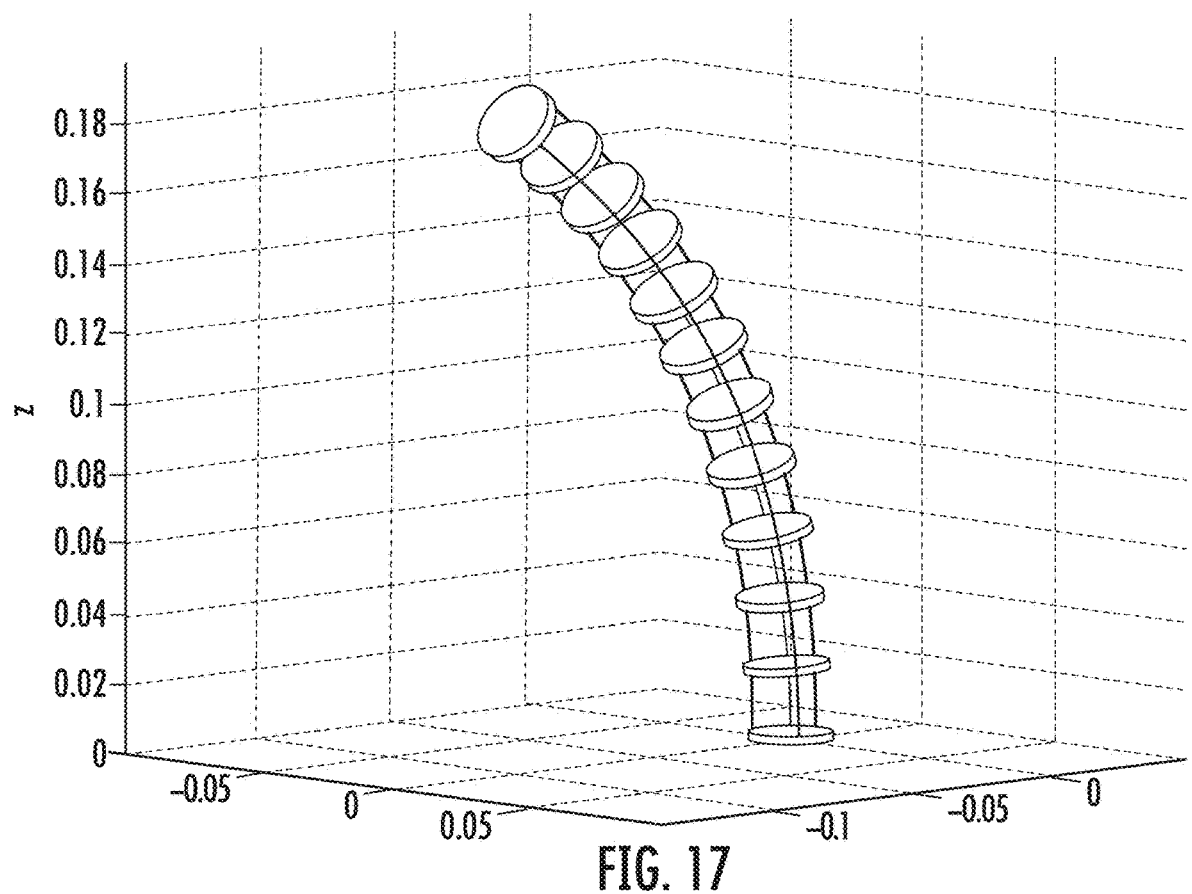
FIG. 17 is the result of model calculations for a continuum robot with pre-curved rods in accordance with the various embodiments.

The variables defining the shape are thus: (a) the amount of elastic structure bending in two directions and torsion within a segment (three variables per segment) and (b) the amount of torsion per segment in each rod (one variable per rod per segment). The elastic spring energy stored in the device and the total lengths of all rods can both be computed using this set of variables. To find the device shape one can then calculate the values of the variables which minimize the stored energy, subject to the constraints that the rod lengths are equal to their specified values. An example of the model's calculation of the shape of the device with pre-curved rods for a certain combination of tube translations and rotations is shown in FIG. 17.

The variables defining the shape may be determined by an energy minimization problem, wherein the values of the variables are those that provide a minimum of an energy. For example, define according to the preceding discussion the following variables: $u_{iS}$, which represents the curvature of the elastic structure over the ith segment; $u_{ij}$, which represents the curvature of the jth rod over the ith segment; $K_S$, which represents the stiffness matrix of the elastic structure, and is typically a diagonal matrix; $K_j$, which represents the stiffness of the jth rod; and the preformed shapes $u_{iS}^*$ and $u_{ij}^*$ which represent the preformed curvatures of the elastic structure and the rods, respectively. Then, the energy function may be written as $$E_{total} = \sum_{i=1}^{M} L_i \left( (u_{iS} - u_{iS}^*)^T K_S (u_{iS} - u_{iS}^*) + \sum_{j=1}^{N} (u_{ij} - u_{ij}^*)^T K_S (u_{ij} - u_{ij}^*) \right)$$

Note that in this set of variables, the torsions are included implicitly through one of the components of the curvature variables. These variables are constrained by a number r functions, the form of which depends on the exact geometry of the device, which may be written implicitly as $$g_k(u_{1S}, \ldots, u_{MS}, u_{11}, \ldots, u_{MN}) = 0$$

for k ranging from 1 to r. Then, the values of the variables which solve the energy minimization problem may be found with a standard technique such as the method of Lagrange multipliers.

VIII. Strip-Type Rods

Figure 29:
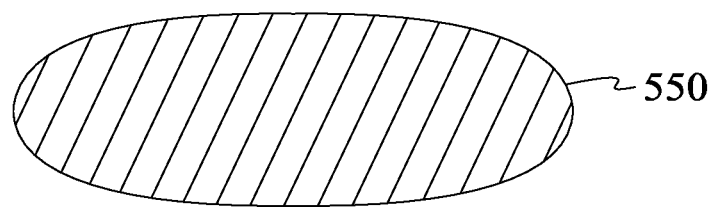
FIG. 29 shows a cross-sectional view of a pre-curved rod being elongated in accordance with one embodiment.

In the previous embodiments, it is generally assumed that the cross-section of the rods is substantially circular or substantially a regular polygon. However, the various embodiments are not limited in this regard. In some embodiments, the rods can have an elongated or oblong cross-section so as to form a strip, i.e., a cross-section other than a circle or a regular polygon. In such embodiments, the cross-section is substantially longer in a first direction than in a second direction perpendicular to the first direction. FIG. 29 shows a cross-sectional view of a pre-curved rod 550 being elongated according to one embodiment. For example, in certain embodiments the strips can be formed by using a rectangular profile.

Figure 28:
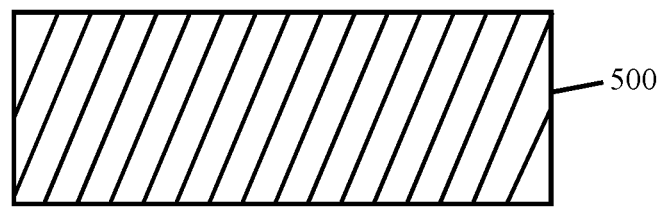
FIG. 28 shows a cross-sectional view of a pre-curved rod in accordance with one embodiment.

Such a configuration offers a number of potential advantages and can be used with straight or pre-curved rods. FIG. 28 shows a generally elongated cross-sectional view of a pre-curved rod 500 being rectangular according to one embodiment. First, strip-type rods allow rods to be thin in one cross sectional dimension. Such a configuration allows strip-type rods to achieve higher curvatures than wire-shaped rods before reaching their strain limit. Second, by being thicker in the other cross sectional direction, strip-type rods can resist loads in the other direction extremely well. This becomes important in the context of continuum robots and endoscopes, which are typically not good at resisting loads normal to their bending plane. Thirds, strip-type rods allow for scalability. In particular, such rods offer a greater surface area for fastening tips to an end disc. Such a configuration is advantageous since the first point of failure in the devices of the various embodiments is likely to be the attachment point between an end of a rod and the disc it is attached to.

Figure 18:
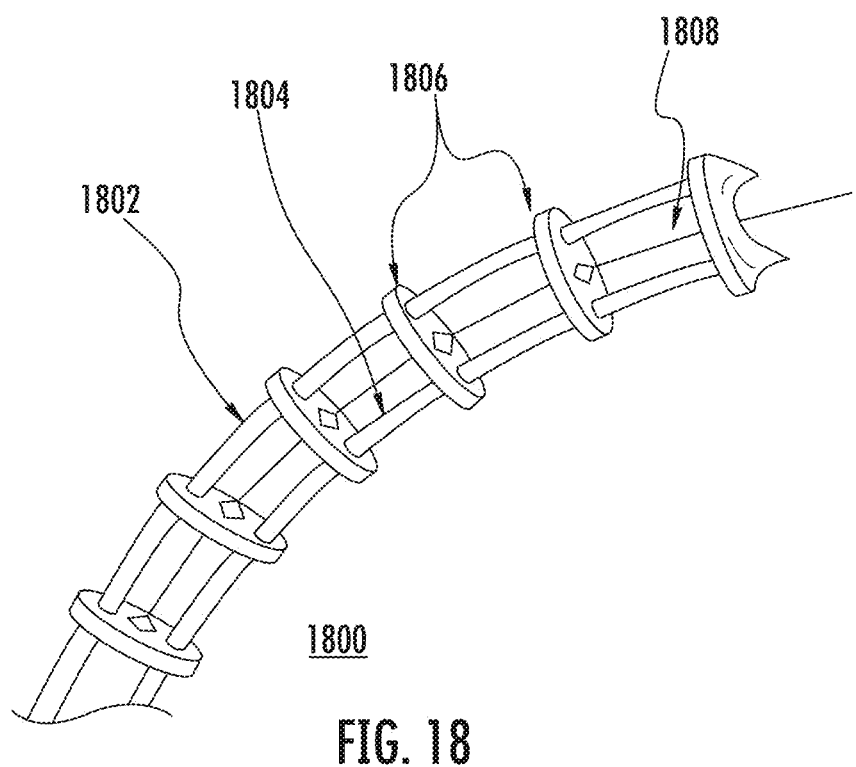
FIG. 18 shows an exemplary device illustrating the use of strip-type rods in accordance with the various embodiments.

An exemplary device 1800 illustrating the use of strip-type rods is shown in FIG. 18. As shown in FIG. 18, the device 1800 is a continuously flexible mechanism, consisting of two elastic strip-type rods 1802, 1804. In the exemplary device 1800 of FIG. 8, these rods are made from nitinol. However, in other embodiments, other elastic materials could be used as well. In device 1800, the rods 1802, 1804 are constrained to remain a fixed distance from one another. As shown in FIG. 18, this is accomplished by passing the rods 1802, 1804, through a series of small spacer discs 1806, attached to an elastic support member 1808 so as to maintain even spacing between the support discs 1806. In the exemplary device 1800, the discs 1806 are 10 mm in diameter. The rods 1802, 1804, are formed using strips that are 0.33 mm thick and 3.3 mm wide, and are pre-curved into circular arcs. The device is shown in its undeflected, "home" position.

Note that other mechanisms could be used to maintain the spacing of the support discs. That is, mechanisms other than the elastic support member. For example, the strip-type rods 1802, 1804 themselves can not only serve to actuate bending in the device 1800, but can also be used to provide structural support within the device 1800. Bending actuation is achieved by pushing one of rods 1802, 1804 in by a fixed distance while pulling the other one of rods 1802, 1804 out by an equal distance. In such embodiments, the rods 1802, 1804 would not be configured to allow them to be individually axially rotated while leaving the rest of the device 1800 in place. However, axial rotation of the device 1800 can be achieved by axially rotating the device 1800 at its base.

In the various embodiments, the strips for rods may be straight or may be pre-curved. Thus, device 1800 can achieve extremely high curvatures by biasing the workspace. Note that the strip-type rods can be pre-curved into circular or non-circular profiles.

The use of thin flexible strips (i.e. elements with a rectangular cross-section in which one dimension is significantly greater than the other) offers several advantages over other flexible elements, which are outlined below.

First, the use of strips over other types of wires or other flexible shapes significantly increases the achievable curvature of the mechanism. This is because, in long beams, the achievable radius of curvature is a function of the thickness of the cross-section of the short dimension. The curvature is limited by a maximum allowable amount of strain in the material (typically the maximum strain before permanent deformation occurs, or some fraction thereof if a factor of safety is incorporated). The maximum strain occurring in a bent beam of a symmetrical cross-section is found by:

$$\text{max bending strain} = \frac{\text{thickness}}{2(\text{radius of curvature})} \quad (29)$$

Based on this, the achievable radius of curvature for a given maximum strain is:

$$\text{achievable radius of curvature} = \frac{\text{thickness}}{2(\text{allowable strain})} \quad (30)$$

Thus, as the thickness of the beam decreases, a smaller radius of curvature becomes achievable.

Figure 19:
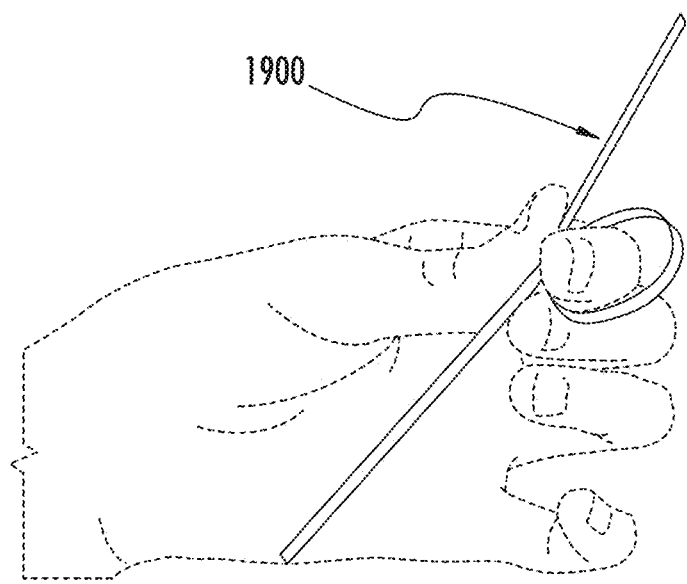
FIG. 19 shows a photograph of straight strip in accordance with the various embodiments bending to a tight curvature.

For a rod (or other non-strip-type member) of the same bending stiffness in the direction of "preferred" bending of the strip (see the following section), the diameter of the rod is approximately 2 times the thickness of the strip (assuming a width-to-thickness ratio of 10:1). Thus, for the equivalent rod, the smallest achievable radius of curvature would be double that of the strip (in other words, the strip would be able to reach twice the curvature the rod would be able to reach, where curvature is the inverse of radius of curvature). For example, FIG. 19 shows a photograph of straight strip 1900 of superelastic nitinol (0.33 mm thick and 3.3 mm wide), easily bending to a tight curvature. The high recoverable strain of superelastic nitinol makes it a useful material in the design of continuously flexible mechanisms, yet in principle any material that can achieve sufficient recoverable strain to satisfy application requirements may be used.

Another advantage of strip-type rods is their ability to achieve different bending stiffnesses in different directions. Using the same beam bending theory employed in the previous section on achievable curvatures, one can observe that a flat strip cross-section rod offers a substantially larger transverse stiffness (i.e. resistance to deflection by loads applied normal to the thin edge of the strip) than a circular cross-section with a bending stiffness equivalent to that of the strip in its direction of "preferred" bending. The stiffness of the rod is related to the modulus of elasticity and the moment of area by $$K=EI \quad (31)$$

where K is the bending stiffness, E is the modulus of elasticity and I is the moment of area. For a rectangular cross-section of width w and thickness t, the moment of area for bending in each direction is:

$$I_{preferred} = \frac{1}{12}t^3 w \quad (32)$$

$$I_{transverse} = \frac{1}{12}tw^3 \quad (33)$$

Now take for example a strip-type member, such as a rod described above, for which the width is ten times the thickness (w=10t), as in the case of the rods shown in FIG. 18. The moment of area expressions can then be written as:

$$I_{preferred} = 0.833t^4 \quad (34)$$

$$I_{transverse} = 83.3t^4 \quad (33)$$

Thus, a strip-type member with a 10:1 width-to-thickness ratio is 100 times stiffer in the transverse direction than it is in the direction of preferred bending. In contrast, for a circular cross-section rod there is no way to achieve high transverse bending stiffness relative to the bending stiffness in the preferred bending direction, since bending stiffness will necessarily be symmetric for a rod with circular cross section.

Ability to increase torsional stiffness of the device

Use of strip-type rods also provides a way to increase the overall device's torsional stiffness, which is another noteworthy benefit. The wide cross-section of each strip provides a moment arm to resist torque as the strip-type rods press against the edges of the slits in the spacer discs. This means that in comparison with a wire-type rod mechanism, the strip-type design will be much more resistant to twisting under external loading. This is especially important as the lack of torsional stiffness is one of the major challenges associated with existing backbone-based designs.

Yet another advantage of strip-type rods is improved miniaturizability. The use of strip-type rods results in increased surface area of the rods compared to wire-type rods. Often in manufacturing, it is necessary to fabricate continuum robots and similar mechanisms at an increasingly small scale. However, a key limiting factor is simply the amount of surface area for attachment of rods to other structures. For example, the amount of surface area glue can adhere in order to attach a rod to a spacing disc. A circular cross section, by definition, has a minimal perimeter for a given cross sectional area. In contrast, so a strip-type rod will always have more surface area to which glue can be applied, and potentially much more if the rod's cross section has a large aspect ratio.

Still another advantage is simplicity in actuation and control. Control of devices including strip-type rods will not require a complex robotic actuation system or a complex method of control, as in many continuum mechanisms. Rather, a simple geometrically derived model effectively describes the actuation of the mechanism. This model is based on the property that the mechanism remains in constant curvature, i.e. that it remains in a circular arc as it is actuated.

In operation, the pose of the mechanism can be described by two variables: bending of the mechanism (which can be equivalently described either by a radius of curvature, r, or the corresponding angle subtended by the arc of the mechanism, $\theta$), and the axial rotation of the robot (described by an angle measured from some nominal or "home" position of the mechanism, $\phi$). These variables constitute the configuration space of the mechanism. The variables used to define how the mechanism is actuated are the displacements of the two strip-type rods ($\delta_o$ for the outer rod and $\delta_i$ for the inner rod), and the rotation of the mechanism's base (the same $\phi$ previously defined). These variables constitute the actuation space of the mechanism.

The following relationship between the length of the centerline of the mechanism L and the radius of curvature r and $\theta$ holds true as the mechanism moves: $L=r\theta$. The length L remains constant during actuation. The lengths of the inner and outer rods are found using the same relationship to be:

$$L_o = (r+D)\theta = L + D\theta \quad (36)$$

$$L_i = (r-D)\theta = L - D\theta \quad (37)$$

where D is the distance from each strip to the centerline, i.e. half the distance between the strips. When the mechanism is in its nominal configuration, the lengths are functions of the nominal radius of curvature and angle, such that $$L_{o,nom} = (r_{nom}+D)\theta_{nom} = L + D\theta_{nom} \quad (38)$$

$$L_{o,nom} = (r_{nom}-D)\theta_{nom} = L - D\theta_{nom} \quad (39)$$

The variables of the extension and retraction of the rods ($\delta_i$ and $\delta_o$) are found to be the difference between each length for a given curvature and the length of the strip in its nominal curvature, i.e.

$$\delta_o = \Delta L_o = L_o - L_{o,nom} = (\theta - \theta_{nom})D = +D\Delta\theta \quad (40)$$

$$\delta_i = \Delta L_i = L_i - L_{i,nom} = -(\theta - _{nom})D = -D\Delta\theta \quad (41)$$

implying that the required changes in length of the inner and outer rods are simply equal but opposite. Thus, a single variable $\delta$ can be used to describe both $\delta_i$ and $\delta_o$ by:

$$\delta = \delta_o = -\delta_i \quad (42)$$

This one-to-one coupling of the extension and retraction of the two rods implies that the relationship can easily be enforced in software for robotically controlled systems, or could be enforced through a mechanical coupling of the two translations, making it possible to use the mechanism in a manual tool.

Figure 20:
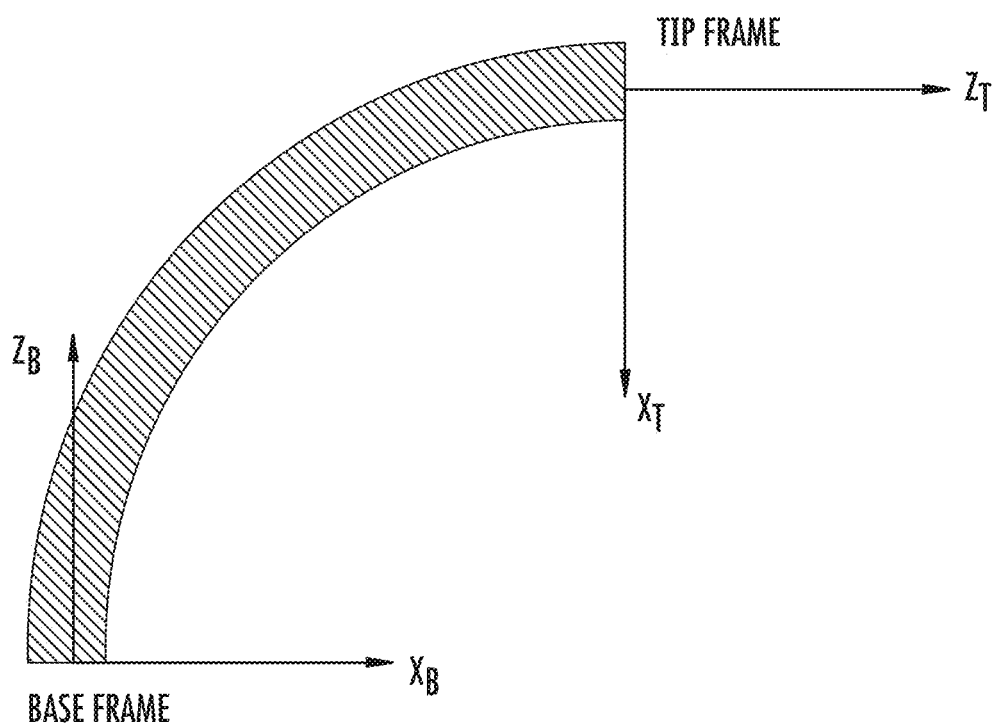
FIG. 20 shows the coordinate frames used in modeling kinematics of a device in accordance with the various embodiments.

The rotational degree-of-freedom is fully described by the angle $\phi$, which can be used interchangeably between the actuation space and configuration space variable. Coordinate frames used in modeling kinematics of the device can be defined as in FIG. 20. Given the coordinate frames defined in FIG. 20, the homogeneous transformation describing the tip frame with respect to the base frame for bending only ($\phi=0$) is:

$$T_\theta = \begin{bmatrix} \cos\theta & 0 & \sin\theta & \frac{L}{\theta}(1-\cos\theta) \\ 0 & 1 & 0 & 0 \\ -\sin\theta & 0 & \cos\theta & \frac{L}{\theta}\sin\theta \\ 0 & 0 & 0 & 1 \end{bmatrix} \quad (43)$$

Similarly, the following transformation describes the motion for rotation only ($\theta = \theta_{nom}$):

$$T_\phi = \begin{bmatrix} \cos\phi & -\sin\phi & 0 & 0 \\ \sin\phi & \cos\phi & 0 & 0 \\ 0 & 0 & 1 & 0 \\ 0 & 0 & 0 & 1 \end{bmatrix} \quad (44)$$

The overall transformation is a combination of these two transformations:

$$T_T^B = T_\phi T_\theta \quad (45)$$

Multiplying this expression out fully and substituting in the relationships between the configuration variables and the actuation variables gives the overall transformation in terms of the actuation variables as follows:

$$T_T^B = \begin{bmatrix} \cos\phi\cos\left(\theta_{nom}+\frac{\delta}{D}\right) & -\sin\phi & \cos\phi\sin\left(\theta_{nom}-\frac{\delta}{D}\right) & \frac{-DL\cos\phi}{\delta+D\theta_{nom}}\left(\cos\left(\frac{\delta}{D}\right)-1\right) \\ \sin\phi\cos\left(\theta_{nom}+\frac{\delta}{D}\right) & \cos\phi & \sin\phi\sin\left(\theta_{nom}+\frac{\delta}{D}\right) & \frac{2DL\sin\phi}{\delta+D\theta_{nom}}\left(\sin^2\left(\frac{\delta+D\theta_{nom}}{2D}\right)\right) \\ -\sin\left(\theta_{nom}+\frac{\delta}{D}\right) & 0 & \cos\left(\theta_{nom}+\frac{\delta}{D}\right) & \frac{DL}{\delta+D\theta_{nom}}\sin\left(\theta_{nom}+\frac{\delta}{D}\right) \\ 0 & 0 & 0 & 1 \end{bmatrix} \quad (46)$$

This transformation can be used to easily compute the hybrid Jacobian for differential inverse kinematics.

IX. Parallel Rod Robots and Maniplators

The preceding discussion assumes the presence of elastic structure to support a platform or disc at the distal end of a continuum robot or other device. However, the various embodiments are not limited in this regard. In particular, multiple rods, attached in parallel to a platform or end disc, can provide all the support needed by such a platform. Thus, a parallel continuum manipulator can be defined. Such parallel continuum manipulators have the potential to inherit some of the compactness and compliance of continuum robots while retaining some of the precision, stability, and strength of rigid-link parallel robots, yet they represent a relatively unexplored area of the broad manipulator design space.

A. Concept and Motivation

Figure 21:
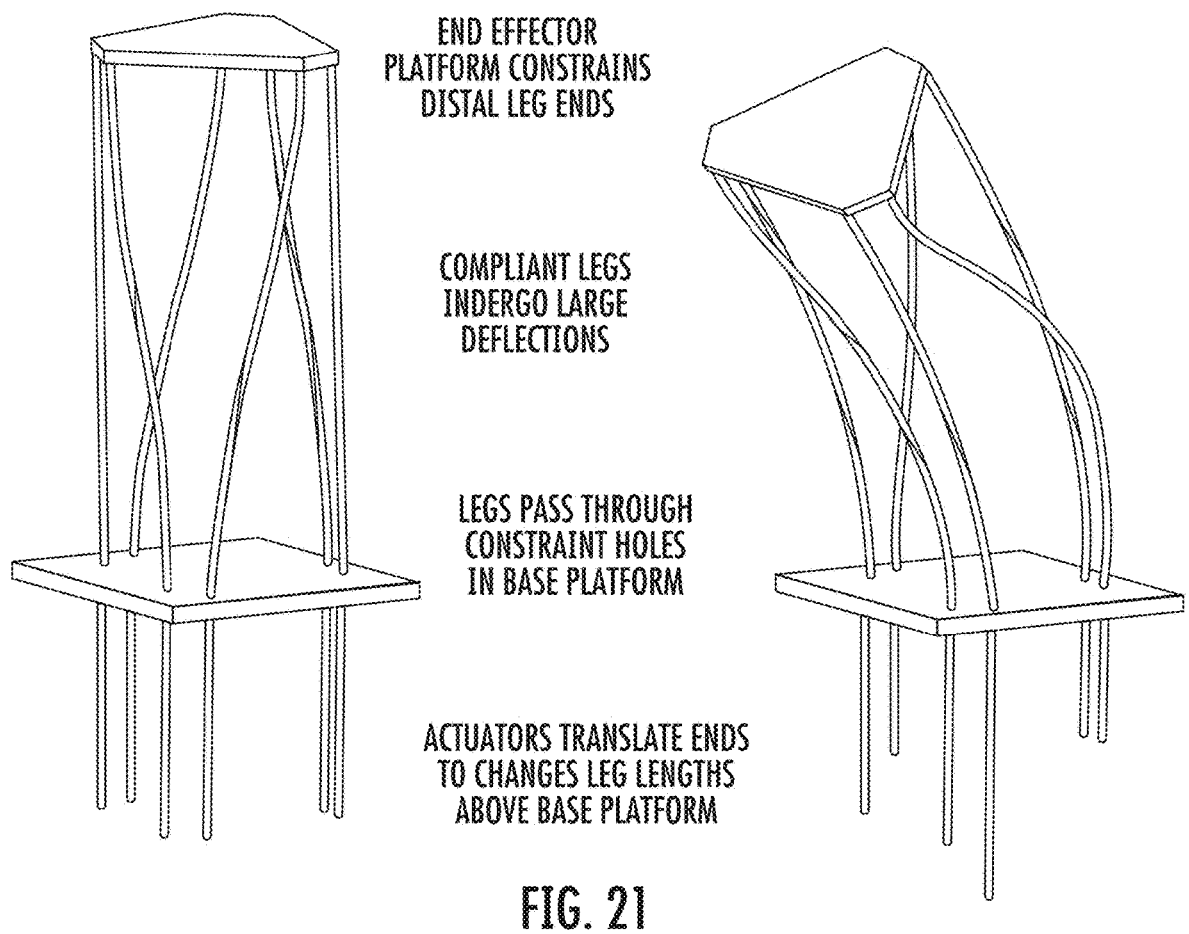
FIG. 21 shows the basic design paradigm of a parallel continuum robot in accordance with the various embodiments.

The basic design paradigm of a parallel continuum robot is illustrated in FIG. 21. In particular, FIG. 21 schematically illustrates the parallel continuum design paradigm utilizes the translation of flexible rods or legs between constrained points to create large deflections in each of the flexible legs. In some embodiments, some or all of the legs can be strip-type rods, as discussed above. The distal ends of the multiple compliant legs are connected in some pattern to an end piece to effect a platform, and the base of each leg is independently translated by an actuator at its proximal end. There may also be some additional constraints on the relative positions of the rods at a certain point (e.g. linear bearings where the rods pass through a base platform). One can conceive of several different variations of parallel continuum robot designs. As with rigid-link parallel manipulators, kinematic behavior is defined by the number of legs and the types of actuation and constraints at each end, which could vary from spherical to clamped joints (our prototype manipulator in FIG. 3 uses clamped joints). The elastic legs themselves could be initially straight or have generally pre-curved stress free states, which could alter the kinematic properties of the device. Using tubes for the legs would allow wires or other infrastructure to be passed through their hollow center channels to the distal platform in order to actuate a gripper or other end effector. Using tubes would also enable hybrid "stacked" designs to be constructed (similar to multi-segment, snake-like designs, except with more degrees of freedom per segment) where the legs of a secondary parallel continuum mechanism extend out the ends the tubes through the distal platform of the primary mechanism.

In comparison to serial continuum robots, parallel continuum designs are likely to have higher payload capacity and accuracy/repeatability. Compared to rigid-link parallel manipulators, they may exhibit greater compliance, larger workspace, and easier miniaturization to the scale of a few millimeters in diameter or smaller. Their inherent mechanical compliance and low mass due to off-loading of the actuators can provide an important safety feature wherever parallel robots need to interact with humans. In the field of endoscopic robotic surgery, parallel continuum manipulators have the potential to provide precise, multi-DOF motion in a simple, compact, and short mechanism at the tip of an endoscope. This capability may be useful for manipulating objects within highly confined spaces where a long slender body would be constrained by anatomical structures. In these cases, access to the site could be gained through flexible endoscopy, and then a parallel continuum device could provide fine, multi-DOF motion at the tip location (actuated by rods passing through hollow channels).

B. Prototype Design And Construction

Figure 22:
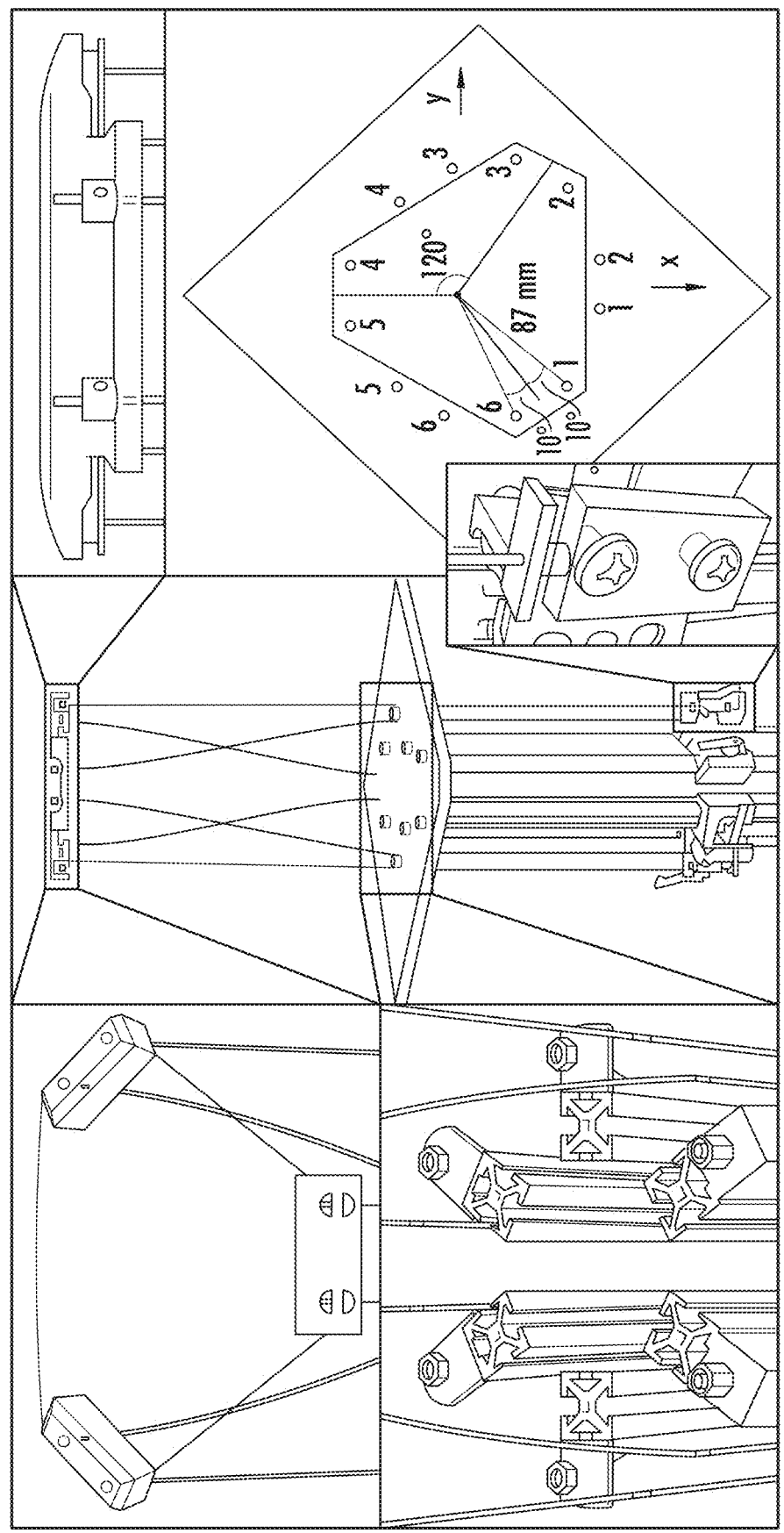
FIG. 22 shows an exemplary parallel continuum manipulator prototype structure in accordance with the various embodiments.

In this section described is the construction of a parallel continuum manipulator prototype structure designed to show proof-of-concept and study parallel continuum robot behavior. This is shown in FIG. 22. In FIG. 22, the middle picture shows our prototype parallel continuum manipulator constructed for initial proof of concept and evaluation of our modeling approach. Close-up views of the base and end platforms are shown to the left in FIG. 22. The dimensions and patterns of the base plate pass-through holes and the top platform connection points are detailed to the right in FIG. 22. The lengths of the compliant legs between the two platforms are actuated by manually translating linear slides connected to the rod ends below the base platform.

The prototype has six compliant legs connected in a similar arrangement to the legs of a 6-DOF rigid-link Stewart-Gough platform, and each leg can be manually actuated. The legs consist of 1.3 mm diameter spring steel music wire (ASTM A228) with an estimated Young's modulus of 207 GPa and Poisson's ratio of 0.305. As shown in FIG. 22, these rods are connected to an end-effector plate of clear 1=16 inch acrylic via 3=8 inch OD shaft collars constrained in channels within small blocks attached to the plate. The rods are routed through holes in the base plate, and the proximal ends are connected to linear slide carriages in the same fashion. The carriages translate along T-slotted aluminum rails (80/20® Inc.) that are bolted in a hexagonal pattern to the base plate. The linear slide carriages can be manually repositioned and locked in place with a brake so that the length of each rod between the base plate and the end plate can be actuated independently.

The connection locations of the 6 flexible legs are arranged in a conventional radial hexapod pattern of 3 pairs of rods spaced 120° apart at a radius of 87 mm. As depicted by the numbers in FIG. 22, the proximal holes for rods 1 and 2 are paired together (with a total separation of 20°), while at the end plate the connections for rods 2 and 3 are paired together. The same pattern follows for the other pairs of wires. Rods 3 and 4, and 5 and 6 are paired at the base plate, while 4 and 5, and 6 and 1 are paired at the distal end. In the neutral configuration shown in FIG. 4 with all leg lengths equal, this connection pattern causes the top plate to be rotated by 60° with respect to the hole pattern in the base plate and causes all of the rods to bend from their naturally straight state.

C. Modeling Approach

Adopted is a kinematic modeling approach for parallel continuum robots that is based on classical Cosserat rod mechanics. The framework outlined in the following subsections addresses the forward and inverse kinematics and statics problems.

i. Cosserat Rod Equations

The shape of each component rod in the robot is defined by its position $p_i(s_i) \in \mathbb{R}^6$ and material orientation $R_i(s_i) \in SO(3)$, forming a material-attached reference frame $$g_i(s_i) = \begin{bmatrix} R_i(s_i) & p_i(s_i) \\ 0 & 1 \end{bmatrix} \in SE(3)$$

as a function of arc length $s_i \in \mathbb{R}$ measured from the proximal platform. The position and orientation evolve along the length of the rod according to kinematic variables $v_i(s) \in \mathbb{R}^6$ and $u_i(s) \in \mathbb{R}^3$, which describe the linear and angular rates of change expressed in local or body frame coordinates of the material frame as follows:

$$p_i' = R_i v_i,$$

$$R_i' = R_i \hat{u}_i, \quad (47)$$

where ' denotes a derivative with respect to $s_i$, and $\hat{\ }$ denotes mapping from $\mathbb{R}^6$ r to so(3) as follows, $$\hat{a} = \begin{bmatrix} 0 & -a_3 & a_2 \\ a_3 & 0 & -a_1 \\ -a_2 & a_1 & 0 \end{bmatrix}. \quad (48)$$

$\vee$ is used to denote the inverse mapping of $\hat{\ }$, i.e., $(\hat{u})^\vee = u$.

The rates of change of the internal force vector n and internal moment vector m with respect to the arc length $s_i$ are described by the classical Cosserat rod differential equations of static equilibrium:

$$n_i' = -f_i$$

$$m_i' = -p_i' \times n_i - l_i, \quad (49)$$

where all vectors are assumed expressed in global coordinates, and $f_i$ and $l_i$ are distributed force and moment vectors respectively applied per unit length to rod i. Distributed self weight and any other external forces are straightforward to include within $f_i$ and $l_i$.

The kinematic variables $v_i$ and $u_i$ are related to material strain (shear, extension, bending, and torsion) and can be used to calculate the internal force and moment vectors (denoted by vectors n and m respectively and expressed in global coordinates) via a material constitutive law. For the present, we use a linear constitutive relationship of the following form, $$n_i = R_i K_{se,i}(v_i - v_i^*),$$

$$K_{se,i} = \begin{bmatrix} A_i G_i & 0 & 0 \\ 0 & A_i G_i & 0 \\ 0 & 0 & A_i E_i \end{bmatrix}$$

$$m_i = R_i K_{bt,i}(u_i - u_i^*),$$

$$K_{bt,i} = \begin{bmatrix} E_i I_i & 0 & 0 \\ 0 & E_i I_i & 0 \\ 0 & 0 & J_i G_i \end{bmatrix}$$

(50)

Where $v_i^*$ and $u_i^*$ are the kinematic variables of the rod in an assigned stress free reference state. For an initially straight rod, appropriate reference state variables are $v_i^* = [0\ 0\ 1]^T$ and $u_i^* = [0\ 0\ 0]^T$. The matrices $K_{se,i}$ and $K_{bt,i}$ here contain the stiffness terms for a radially symmetric rod cross-section which could vary with arc length, involving the area $A_i$, Young's modulus, $E_i$, the shear modulus $G_i$, the second area moment $I_i$ (about the local x and y axes), and the polar area moment $J_i$ about the local z axis.

Thus, for each rod, the equations discussed above can be used to form a system of differential equations that describes the evolution of the state variables $p_i$, $R_i$, $m_i$, and $n_i$ with respect to $S_i$.

ii. Boundary Conditions for Forward Kinematics

Each rod or tube in a parallel continuum robot is independently described by the system of differential equations above. However, the boundary conditions of each system are coupled because of the physical constraints inherent to the robot structure.

For the prototype robot design which describe herein, the proximal end of each rod is clamped with a set-screw shaft collar constrained within a groove in acrylic block, and each rod subsequently passes through a cylindrical hole in the base platform as shown in FIG. 3. This design constrains the position pi and the rod tangent vector at the base platform while allowing rotational freedom about the tangent axis so that no torsional moment can be supported. Thus, the torsional moment is set to zero at the base of each rod and $R_i(0)$ is expressed as a rotation about the global z-axis by some angle $\theta_i$ as follows:

$$m_{iz}(0) = 0 \quad (51)$$

$$R_i(0) = \begin{bmatrix} \cos\theta_i & -\sin\theta_i & 0 \\ \sin\theta_i & \cos\theta_i & 0 \\ 0 & 0 & 1 \end{bmatrix}$$

At the distal end of each rod ($s_i = L_i$), the following conditions of static equilibrium must hold for the top plate:

$$\sum_{i=1}^{n} [n_i(L_i)] - F = 0 \quad (52)$$

$$\sum_{i=1}^{n} [p_i(L_i) \times n_i(L_i) + m_i(L_i)] - p_c \times F - M = 0,$$

where F and M are external force and moment vectors applied at the centroid of the top plate, $p_c$. The clamped connections of the distal end of the rods to the top plate are modeled by setting the material orientations of each rod at $L_i$ equal to each other:

$$[\log(R_i^T(L_i)R_1(L_1))]^\vee = 0 \text{ for } i = 2 \ldots n, \quad (53)$$

where log ( ) is the matrix natural logarithm, which maps SO(3) to so(3), and the $\vee$ operator subsequently maps so(3) to $\mathbb{R}^6$. This forces a common material orientation for all the distal rod ends. Finally, one can write the following equations for the rod end positions.

$$p_1(L_1) - p_i(L_i) - R_1(L_1)(r_1 - r_i) = 0 \text{ for } i = 2 \ldots n, \quad (54)$$

where $r_i$ is the connection position for rod i expressed with respect to the top plate coordinate system. These are analogous to loop closure equations because they are only satisfied when the positions of the rod ends have the same relative positions as the connection pattern in the top plate.

iii. Boundary Conditions for Inverse Kinematics

For the inverse kinematics problem, the boundary conditions given above in (5) and (6) still apply, but the geometric coupling of the rods at the distal platform is simplified by the fact that a desired position and orientation is known. This can be expressed by a constraint on the position and orientation of each distal leg end as follows:

$$[\log(R_i^T(L_i)R_d)]^\vee = 0 \text{ for } i = 1 \ldots n,$$

$$p_d + R_d r_i - p_i = 0 \text{ for } i = 1 \ldots n. \quad (55)$$

where $p_d$ and $R_d$ are the desired position (of the centroid) and orientation of the distal platform. We note that these equations are applied for i=1 . . . n, so there are a total of six more scalar constraint equations to be solved than in the forward kinematics case, and the leg lengths constitute n additional unknowns.

iv. Numerical Computation

A simple shooting method provides an effective way to solve the systems of rod equations subject to these coupled boundary conditions. In this procedure, the unknown boundary conditions at the base of each rod ($n_i(0)$, $m_{ix}(0)$, $m_{iy}(0)$, and $\theta_i$) are guessed (in the inverse kinematics case, the leg lengths Li are included in this set of unknowns). Each system of rod equations is numerically integrated from $s_i=0$ to $L_i$ as an initial value problem using a standard numerical routine such as a Runge-Kutta method, and the boundary condition equations are subsequently evaluated. This process is nested within an optimization loop which iteratively updates the guessed values for the unknown proximal boundary conditions until the distal boundary conditions are satisfied within an appropriate tolerance. This is an efficient and relatively stable method of computation. For the examples shown in the experimental section, convergence was achieved in every case, starting with an uninformed initial guess of zero for all unknown proximal conditions. Computation time was on the order of 10 seconds using unoptimized MATLAB code executed on a typical laptop computer. Computation time decreases to about 1 second if a good initial guess is available, which enables simulation of quasistatic motion since a previous solution can be used as the initial guess for the next iteration.

v. Multiple Solutions and Buckling Behavior

In contrast to rigid-link robots, the forward and inverse kinematics problems for parallel continuum manipulators are both complex (with the potential for multiple solutions possible) due to the large-deflection elastic behavior involved. For the numerical computation strategy above, the set of values for the unknown initial conditions (and leg lengths in the case of inverse kinematics) which satisfies the distal end boundary conditions may not always be unique. In this context, the phenomena of "buckling" describes the sudden transition of one valid solution to another one, which may occur when a particular equilibrium solution becomes unstable (or ceases to exist) as the result of a small change in actuation or external loading. The model equations are still valid in these situations, and they contain the ability to accurately describe all possible "buckled" states if the correct solution for the initial conditions is selected. The quasistatic simulation process described above tends to produce the correct solution until a point of instability is reached. The potential for buckling and instability exists for all continuum robots when external loads are considered, and for some designs even without external loading (e.g. concentric-tube robots).

D. Kinematic Simulation and Analysis

Figure 23:
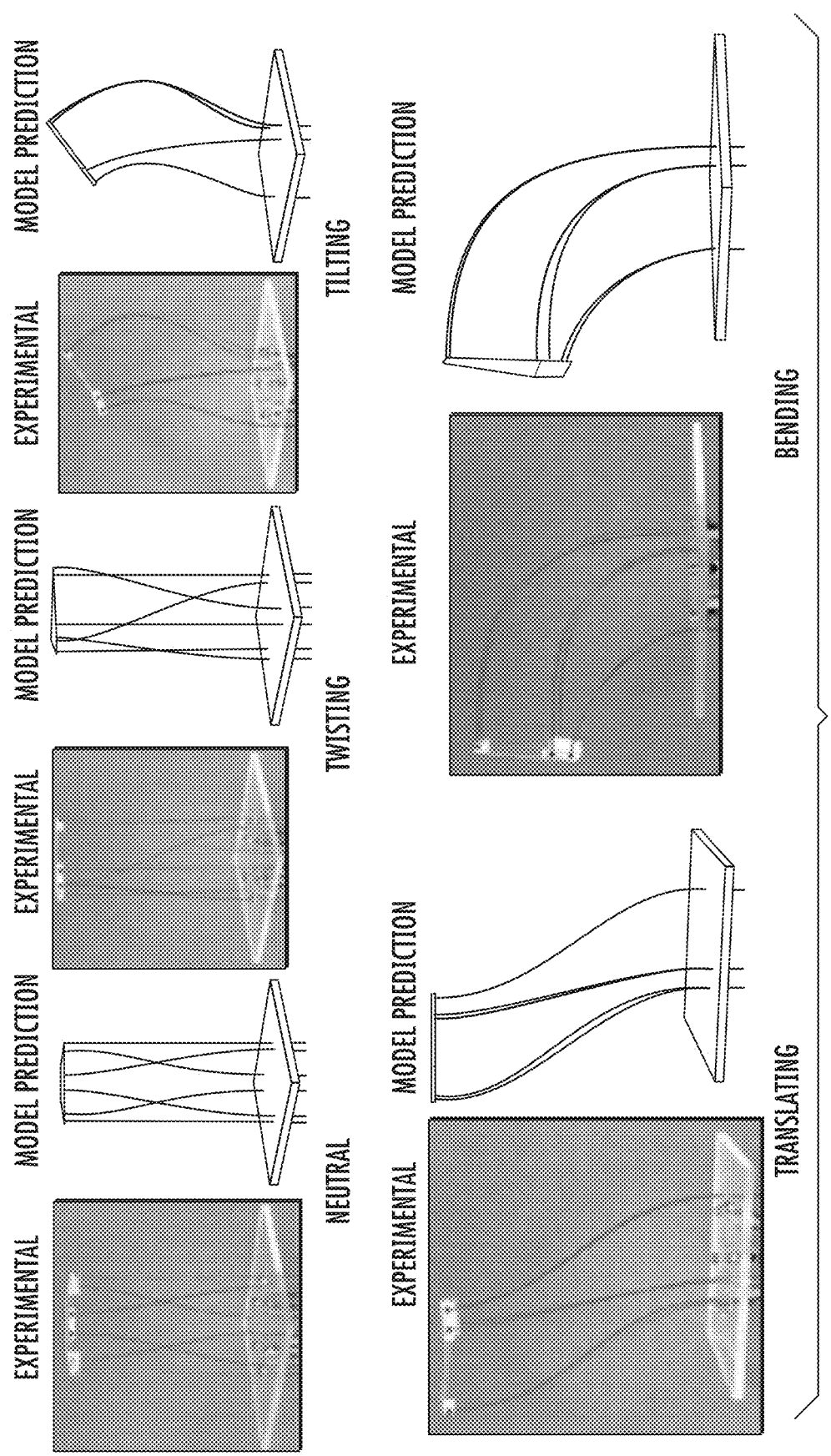
FIG. 23 demonstrates the kinematic degrees of freedom and range of motion of the prototype manipulator structure in accordance with the various embodiments.
Figure 24A:
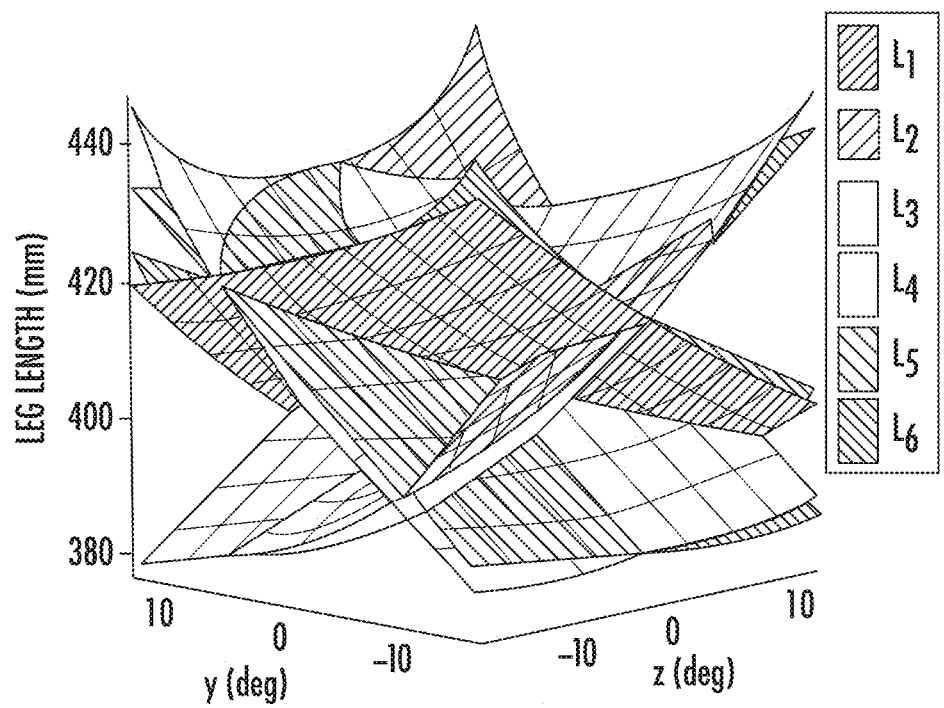
FIG. 24 depicts the inverse kinematic mapping over 3 two-dimensional slices of a workspace.
Figure 24B:
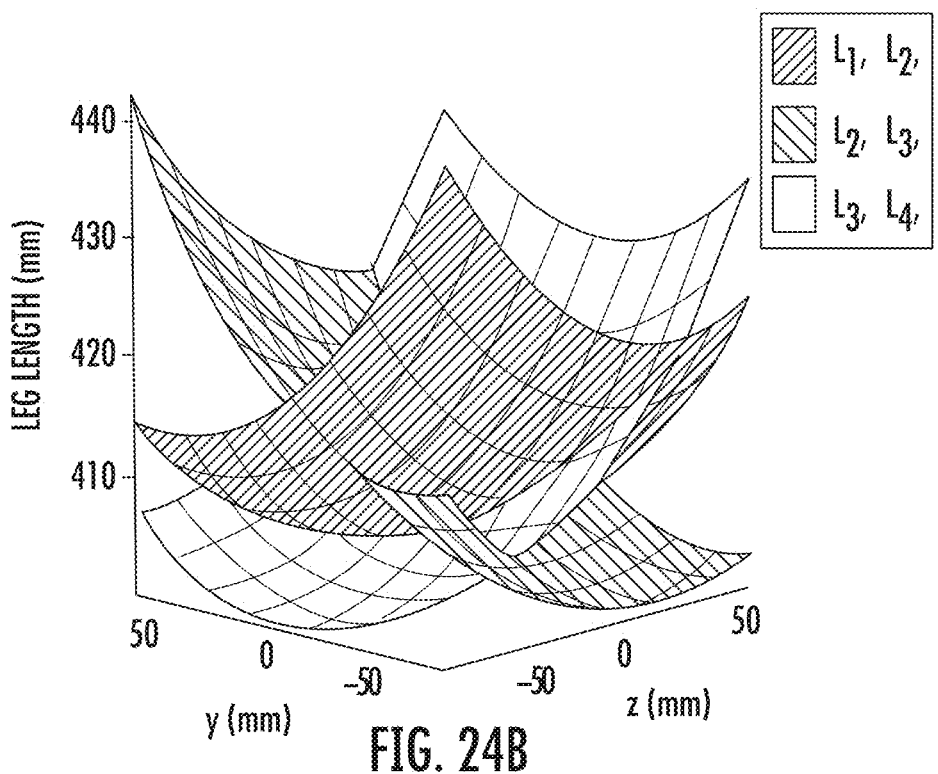
Figure 24C:
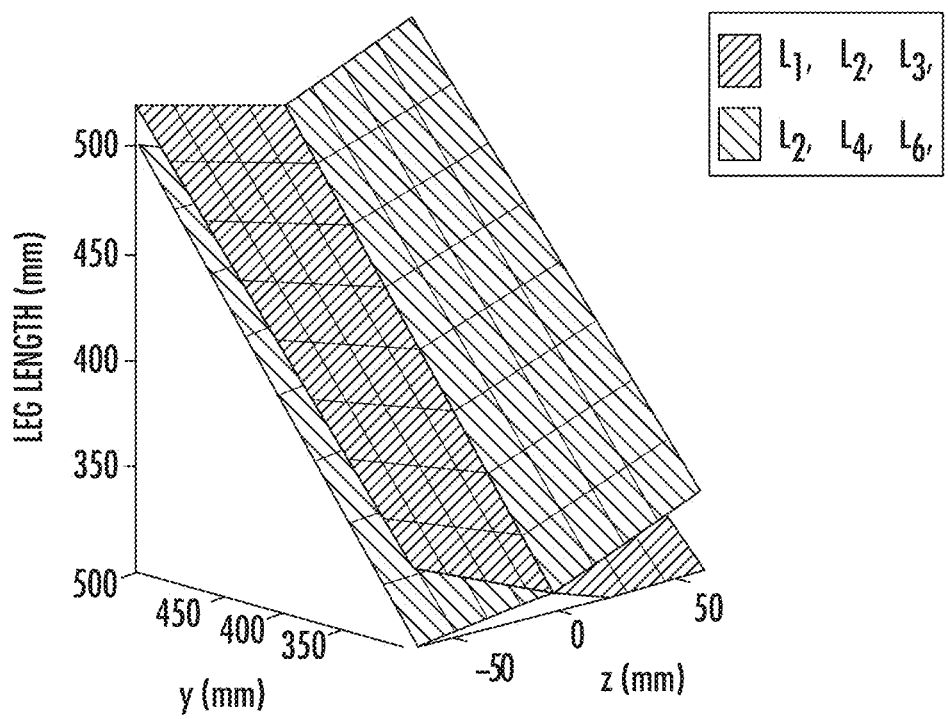
Figure 24D:
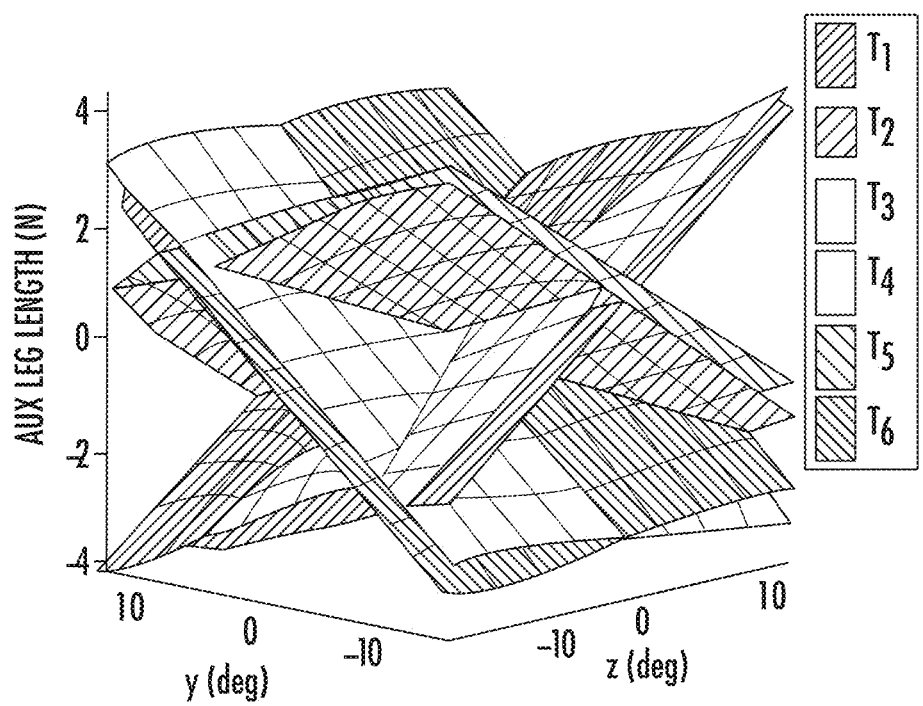
Figure 24E:
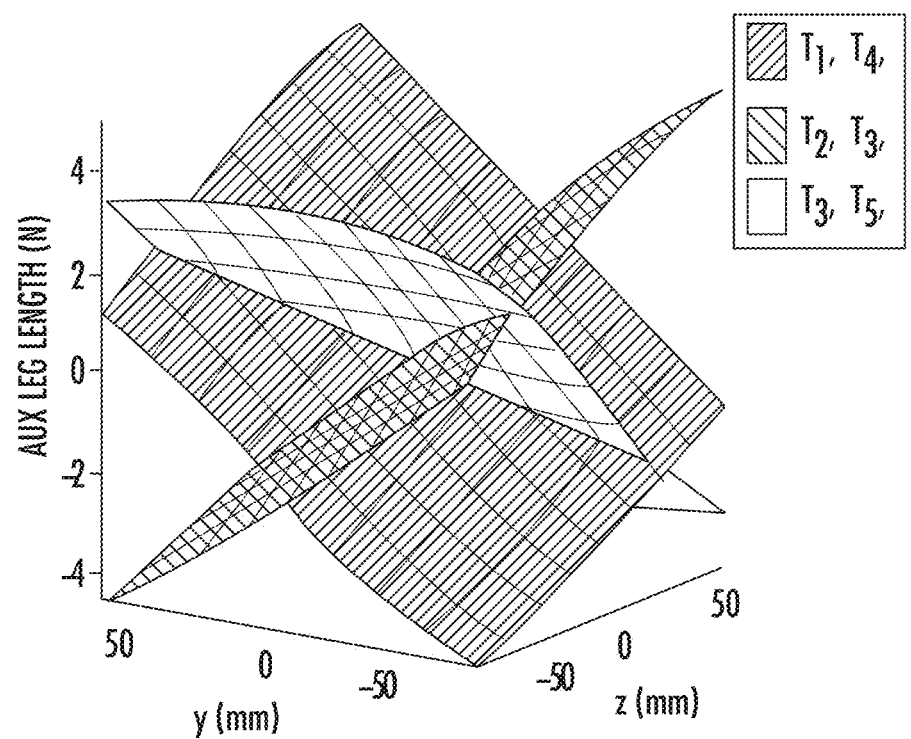
Figure 24F:
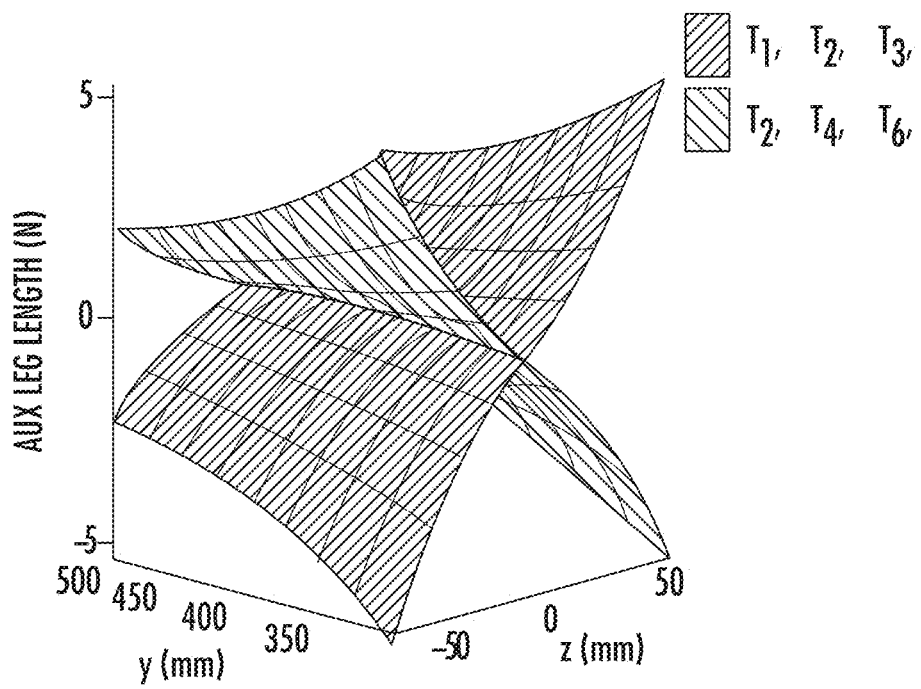

FIG. 23 demonstrates the kinematic degrees of freedom and range of motion of the prototype manipulator structure described herein by showing the manipulator shape in five different configurations. In particular, FIG. 23 shows photographs of five experimental configurations, demonstrating the ability of our prototype parallel continuum manipulator to execute axial twist, transverse tilt, translation, and bending (simultaneous translation and tilt). To the right of each experimental photograph, a MATLAB rendering of the rod-mechanics-based kinematic model prediction for the same actuator configurations is shown.

With all leg lengths equal, the robot is in a straight, neutral state, which can be raised or lowered by equal translation of the legs. By extending legs 2, 4, and 6, the distal platform twists about the z-axis. Translating legs 4 and 5 causes the platform to tilt, and translating legs 3 and 6 causes translation. A combination of rotation and translation (bending) is achieved by extending legs 4 and 5 while retracting legs 1 and 2. The collection of legs maintains a compact form throughout all these motions, which is encouraging for potential applications in confined spaces. FIG. 23 also shows a rendering of our forward kinematics model solution for these five cases, indicating the feasibility and qualitative accuracy of the modeling approach over a wide range of motion.

To further illustrate the kinematics of the prototype design, the body-frame manipulator is given a Jacobian, $J_b$, which was computed numerically for the prototype manipulator in the neutral configuration (where all leg lengths are 406 mm, and the rotation is aligned with the global reference frame.)

$$J^b = \begin{bmatrix} -1.62 & -1.62 & 1.83 & -0.21 & -0.21 & 1.83 \\ -1.18 & 1.18 & -0.82 & -2.00 & 2.00 & 0.82 \\ 0.17 & 0.17 & 0.17 & 0.17 & 0.17 & 0.17 \\ -0.12 & 0.12 & 0.24 & 0.12 & -0.12 & -0.24 \\ -0.20 & -0.20 & 0.00 & 0.20 & 0.20 & 0.00 \\ -0.65 & 0.65 & -0.65 & 0.65 & -0.65 & 0.65 \end{bmatrix}$$

where the top 3 rows are dimensionless, and the bottom three rows have units of degrees/mm. The matrix is full rank and well-conditioned, indicating that in the neutral configuration, actuators can easily move the top platform in any direction in the 6 DOF space of rigid body motion. In FIG. 24, depicted is the inverse kinematic mapping over 3 two-dimensional slices of the workspace. The figure shows the required leg length and axial tension at the base of each leg as a function of the desired end-effector pose, which is specified by position $p_d=[x\ y\ z]^T$ and orientation $R_d=\exp(\hat{\theta})$, $\theta=[\theta_x\ \theta_y\ \theta_z]^T$. For each slice, two of the six pose variables were varied over a 9×9 grid of values for which the inverse kinematics computation easily converged, while all other pose variables were held constant at their nominal values of $x=y=\theta_x=\theta_y=\theta_z=0$, and $z=400$ mm.

The first case (FIG. 24: (a) and (d)) shows an approximately linear kinematic mapping for desired rotation about the x and y axes. The second case (FIG. 24: (b) and (e)) shows an approximately quadratic leg length mapping and an approximately linear tension mapping for desired translation in the x-y plane. Note that in this case, the required lengths and tensions are identical for legs 1 and 4, 2 and 5, and 3 and 6 respectively. The final case (FIG. 24: (c) and (f)) shows an approximately linear leg length mapping and an approximately cubic tension mapping for desired motion which both rotates about and translates along the global z axis. In this case, the lengths and tensions are identical for legs 1, 3, and 5, and 2, 4, and 6 respectively.

The axial tension at the base of each leg corresponds to the actuator force which would be required to hold the robot in a particular configuration. Over these ranges of motion, moderate forces on the order of 5 N will be required to actuate the structure. A simulation of this kind can be used in the design process to size motors for a particular set of manipulator structural parameters, and to limit the length that the legs extend below the base platform to avoid buckling. One can also compute the output stiffness matrix at the top platform, which maps displacement of the end effector centroid to applied force $dF=Kdp_c$. For the neutral configuration in FIG. 4, the computed stiffness matrix is $$K = \begin{bmatrix} 17 & 0 & 0 \\ 0 & 17 & 0 \\ 0 & 0 & 122 \end{bmatrix} N/mm,$$

while for the bending configuration in FIG. 23, the stiffness matrix is computed to be $$K = \begin{bmatrix} 12.7 & 0 & 12.8 \\ 0 & 0.5 & 0 \\ 12.8 & 0 & 14.5 \end{bmatrix} N/mm,$$

These computations show that the stiffness in the y direction (out of the page for the bending case in FIG. 23), is only about 3% of its value in the straight case, which is consistent with this prototype. Care should be taken when designing and controlling a parallel continuum manipulator to ensure that output stiffness is sufficient for the desired tasks.

V. Experimental Validation

Figure 25:
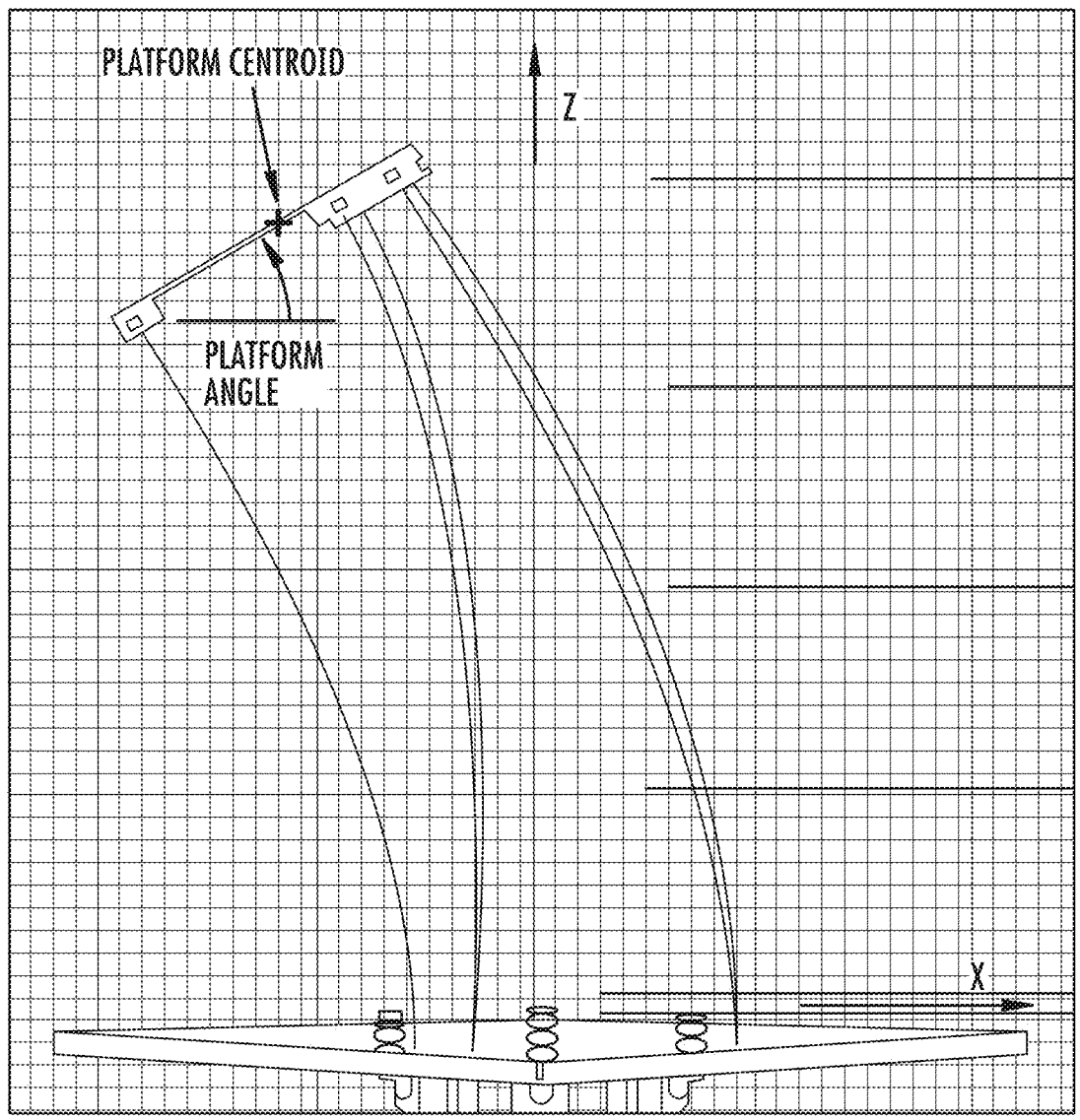
FIG. 25 shows the basic elements of each image that were measured during validation experiments.

A set of model validation experiments was performed by photographing the shape of the prototype manipulator in front of a graph poster in 14 different actuator configurations, which are listed in Table I. FIG. 25 shows the basic elements of each image that were measured, the top platform centroid and orientation in the global x-z plane. The three main measurements taken from the images are the position of the centroid of the end effector plate in the x and z, which is denoted by the marker at the top, and the orientation of the end effector in the x-z plane. The orientation was measured by drawing a line along the end effector edge and then measuring the slope of the line with the grid poster.

These measurements were then compared to our forward kinematics model prediction for each actuator configuration. The photos of these planar cases were taken perpendicular to the graph plane approximately 30 feet away from the robot so that perspective error was minimized.

The resulting differences between the data and the model prediction are presented in Table I. The positional error was calculated as the total Cartesian error in the global x-z plane, and the percent error was calculated as the position error divided by the average leg length for each case. The maximum positional error was 11.74 mm with a 2.89% associated percent error. For the configurations resulting in a change in top platform orientation (7-14 in Table I), angular displacement was measured graphically as shown in FIG. 6, and the maximum angular difference between model prediction and experiment was 3.14 degrees.

TABLE I

EXPERIMENTAL CONFIGURATIONS AND MODEL ERROR (MM)

| # | $L_1$ | $L_2$ | $L_3$ | $L_4$ | $L_5$ | $L_6$ | Error | % Error |
|---|---|---|---|---|---|---|---|---|
| 1 | 406 | 406 | 406 | 406 | 406 | 406 | 3.4 | 0.8 |
| 2 | 386 | 406 | 386 | 406 | 386 | 406 | 6.1 | 1.6 |
| 3 | 426 | 406 | 426 | 406 | 426 | 406 | 2.9 | 0.7 |
| 4 | 406 | 406 | 426 | 406 | 406 | 426 | 8.8 | 2.1 |
| 5 | 406 | 406 | 386 | 406 | 406 | 386 | 7.1 | 1.8 |
| 6 | 406 | 406 | 366 | 406 | 406 | 366 | 5.4 | 1.4 |
| 7 | 406 | 406 | 406 | 386 | 386 | 406 | 7.5 | 1.8 |
| 8 | 406 | 406 | 406 | 366 | 366 | 406 | 10.4 | 2.7 |
| 9 | 406 | 406 | 406 | 426 | 426 | 406 | 8.9 | 2.1 |
| 10 | 406 | 406 | 406 | 446 | 446 | 406 | 7.6 | 1.8 |
| 11 | 426 | 426 | 406 | 386 | 386 | 406 | 7.0 | 1.7 |
| 12 | 446 | 446 | 406 | 366 | 366 | 406 | 10.4 | 2.6 |
| 13 | 386 | 386 | 406 | 426 | 426 | 406 | 9.3 | 2.3 |
| 14 | 366 | 366 | 406 | 446 | 446 | 406 | 11.7 | 2.9 |

Observed was a small amount of flex in the top acrylic plate during the experiments. This unmodeled effect is a source of error between model prediction and actual manipulator shape.

A. Buckling Experiments

Figure 26A:
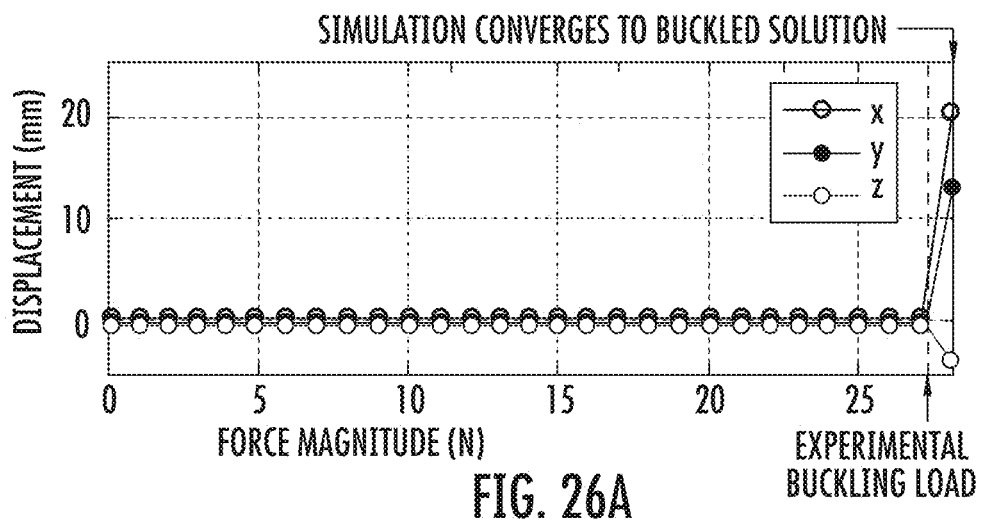
FIGS. 26A, 26B, and 26C show displacements of the top platform centroid in the x, y, and z directions are plotted by using our forward kinematics model to perform quasistatic simulation with an incrementally increasing vertical load for three different manipulator configurations.
Figure 26B:
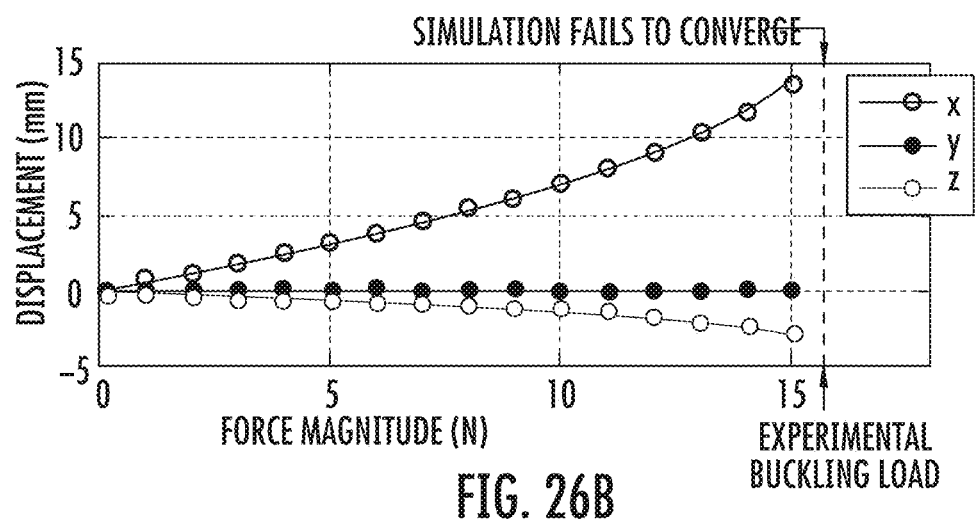
Figure 26C:
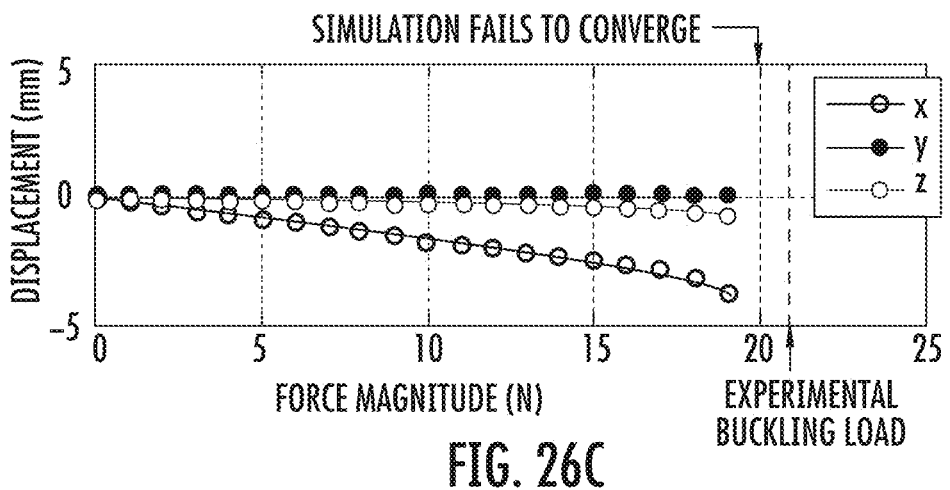

Also experimentally determined was a critical buckling load for the prototype structure in three different actuator configurations, (1, 4, and 5 in Table I, corresponding to a straight neutral case and two translating cases, respectively). Applied was an incrementally increasing force in the negative z direction (down) through the centroid of the top plate until at least one leg in the structure began to buckle. The resulting experimental buckling loads are shown by the black dashed lines in FIGS. 26A-C. FIGS. 26A-C show displacements of the top platform centroid in the x, y, and z directions are plotted by using our forward kinematics model to perform quasistatic simulation with an incrementally increasing vertical load for three different manipulator configurations (1, 4, and 5 in Table I). The dashed lines depict the experimentally determined critical buckling loads for the same cases. In FIG. 26A, the simulation converged to a buckled solution at an applied load very close to the experimentally determined buckling load. In FIGS. 26B and 26C the simulation failed to converge to any solution just prior to when the simulated load would have reached the experimentally determined buckling load.

When running a forward kinematics model simulation with the same incrementally increasing force, the simulation converged to a buckled solution (shown by the sudden large centroid displacement in FIG. 26A at a load close to the experimentally determined buckling load. For configurations 4 and 5 (FIGS. 26B and 26C), the simulation failed to converge to a valid forward kinematics solution just prior to reaching the experimentally determined buckling load, indicating that the buckled mode is not relatively close to the unbuckled state.

X. Exemplary Computer System

Figure 27:
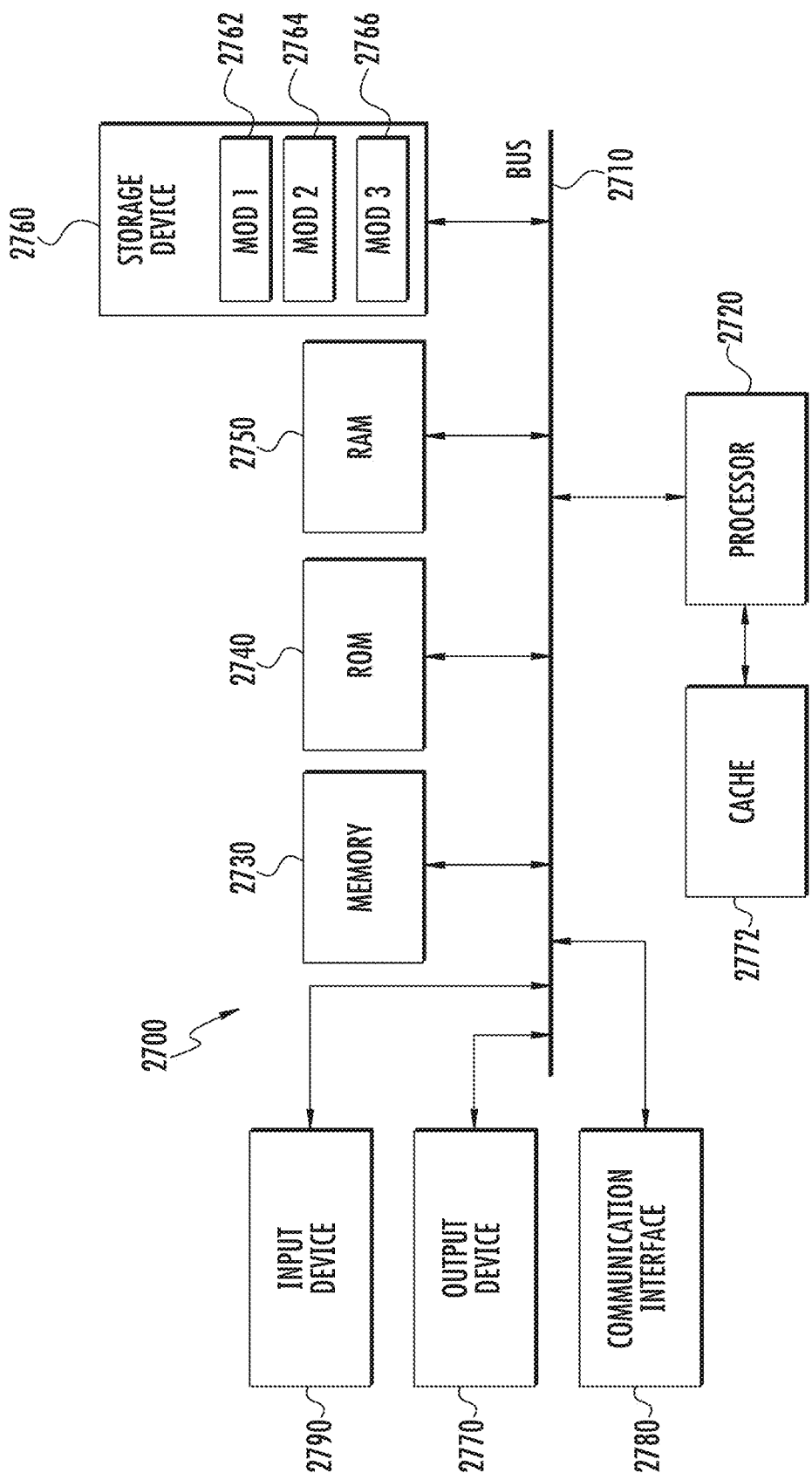
FIG. 27 shows an exemplary computing device 1800 for performing methods and processes in accordance with the various embodiments.

Turning now to FIG. 27, this is shown an exemplary system 2700 includes a general-purpose computing device 2700 for performing one or more of the various methods and processes described above. System 2700 includes a processing unit (CPU or processor) 2720 and a system bus 2710 that couples various system components including the system memory 2730 such as read only memory (ROM) 2740 and random access memory (RAM) 2750 to the processor 2720. The system 2700 can include a cache 2722 of high speed memory connected directly with, in close proximity to, or integrated as part of the processor 2720. The system 2700 copies data from the memory 2730 and/or the storage device 2760 to the cache 2722 for quick access by the processor 2720. In this way, the cache 2722 provides a performance boost that avoids processor 2720 delays while waiting for data. These and other modules can be configured to control the processor 2720 to perform various actions. Other system memory 2730 may be available for use as well. The memory 2730 can include multiple different types of memory with different performance characteristics. It can be appreciated that the disclosure may operate on a computing device 2700 with more than one processor 2720 or on a group or cluster of computing devices networked together to provide greater processing capability. The processor 2720 can include any general purpose processor and a hardware module or software module, such as module 1 2762, module 2 2764, and module 3 2766 stored in storage device 2760, configured to control the processor 2720 as well as a special-purpose processor where software instructions are incorporated into the actual processor design. The processor 2720 may essentially be a completely self-contained computing system, containing multiple cores or processors, a bus, memory controller, cache, etc. A multi-core processor may be symmetric or asymmetric.

The system bus 2710 may be any of several types of bus structures including a memory bus or memory controller, a peripheral bus, and a local bus using any of a variety of bus architectures. A basic input/output (BIOS) stored in ROM 2740 or the like, may provide the basic routine that helps to transfer information between elements within the computing device 2700, such as during start-up. The computing device 2700 further includes storage devices 2760 such as a hard disc drive, a magnetic disc drive, an optical disc drive, tape drive or the like. The storage device 2760 can include software modules 2762, 2764, 2766 for controlling the processor 2720. Other hardware or software modules are contemplated. The storage device 2760 is connected to the system bus 2710 by a drive interface. The drives and the associated computer readable storage media provide non-volatile storage of computer readable instructions, data structures, program modules and other data for the computing device 2700. In one aspect, a hardware module that performs a particular function includes the software component stored in a tangible and/or intangible computer-readable medium in connection with the necessary hardware components, such as the processor 2720, bus 2710, display 2770, and so forth, to carry out the function. The basic components are known to those of skill in the art and appropriate variations are contemplated depending on the type of device, such as whether the device 2700 is a small, handheld computing device, a desktop computer, or a computer server.

Although the exemplary embodiment described herein employs the hard disc 2760, it should be appreciated by those skilled in the art that other types of computer readable media which can store data that are accessible by a computer, such as magnetic cassettes, flash memory cards, digital versatile discs, cartridges, random access memories (RAMs) 2750, read only memory (ROM) 2740, a cable or wireless signal containing a bit stream and the like, may also be used in the exemplary operating environment. Tangible, non-transitory computer-readable storage media expressly exclude media such as energy, carrier signals, electromagnetic waves, and signals per se.

To enable user interaction with the computing device 2700, an input device 2790 represents any number of input mechanisms, such as a microphone for speech, a touch-sensitive screen for gesture or graphical input, keyboard, mouse, motion input, speech and so forth. An output device 2770 can also be one or more of a number of output mechanisms known to those of skill in the art. In some instances, multimodal systems enable a user to provide multiple types of input to communicate with the computing device 2700. The communications interface 2780 generally governs and manages the user input and system output. There is no restriction on operating on any particular hardware arrangement and therefore the basic features here may easily be substituted for improved hardware or firmware arrangements as they are developed.

For clarity of explanation, the illustrative system embodiment is presented as including individual functional blocks including functional blocks labeled as a "processor" or processor 2720. The functions these blocks represent may be provided through the use of either shared or dedicated hardware, including, but not limited to, hardware capable of executing software and hardware, such as a processor 2720, that is purpose-built to operate as an equivalent to software executing on a general purpose processor. For example the functions of one or more processors presented in FIG. 27 may be provided by a single shared processor or multiple processors. (Use of the term "processor" should not be construed to refer exclusively to hardware capable of executing software.) Illustrative embodiments may include microprocessor and/or digital signal processor (DSP) hardware, read-only memory (ROM) 2740 for storing software performing the operations discussed below, and random access memory (RAM) 2750 for storing results. Very large scale integration (VLSI) hardware embodiments, as well as custom VLSI circuitry in combination with a general purpose DSP circuit, may also be provided.

The logical operations of the various embodiments are implemented as: (1) a sequence of computer implemented steps, operations, or procedures running on a programmable circuit within a general use computer, (2) a sequence of computer implemented steps, operations, or procedures running on a specific-use programmable circuit; and/or (3) interconnected machine modules or program engines within the programmable circuits. The system 2700 shown in FIG. 27 can practice all or part of the recited methods, can be a part of the recited systems, and/or can operate according to instructions in the recited tangible computer-readable storage media. Such logical operations can be implemented as modules configured to control the processor 2720 to perform particular functions according to the programming of the module. For example, FIG. 27 illustrates three modules Mod1 2762, Mod2 2764 and Mod3 2766 which are modules configured to control the processor 2720. These modules may be stored on the storage device 2760 and loaded into RAM 2750 or memory 2730 at runtime or may be stored as would be known in the art in other computer-readable memory locations.

XI. Derivation Appendix

A. Nomenclature

\*: Denotes a variable in the reference state.

': Denotes a derivative with respect to s.

^: Coverts $\mathbb{R}^6$ to so(3) and $\mathbb{R}^6$ to $\mathfrak{so}(3)$:

$$u = \begin{bmatrix} 0 & -u_z & u_y \\ u_z & 0 & -u_x \\ -u_y & u_x & 0 \end{bmatrix},$$

-continued $$\begin{bmatrix} \hat{v} \\ \hat{u} \end{bmatrix} = \begin{bmatrix} 0 & -u_z & u_y & u_x \\ u_z & 0 & -u_x & u_y \\ -u_y & u_x & 0 & u_z \\ 0 & 0 & 0 & 0 \end{bmatrix}$$

ˇ: Inverse of the ˆ operation. $(\hat{u})^{\vee} = u$.
s: $\in \mathbb{R}$—Reference length parameter.
p(s): $\in \mathbb{R}^6$—Position of the robot backbone centroid in global frame coordinates.
R(s): $\in SO(3)$—Orientation of the robot backbone material with respect to the global frame.
g(s): $\in SE(3)$—Homogeneous transformation containing R(s) and p(s). (The "body frame")
$r_i(s) \in \mathbb{R}^3$: Position of the $i^{th}$ tendon with respect to the body frame. $r_i(s) = [x_i(s) y_i(s) 0]^T$
$p_i(s)$: $\in \mathbb{R}^6$—Position of the $i^{th}$ tendon in global frame coordinates. $p_i(s) = R r_i(s) + p(s)$.
u(s): $\in \mathbb{R}^6$—Angular rate of change of g with respect to s in body-frame coordinates. $u = (R_T \dot{R})^{\vee}$
v(s): $\in \mathbb{R}^6$—Linear rate of change of g with respect to s expressed in body-frame coordinates. $v = R^T \dot{p}$
n(s): $\in \mathbb{R}^6$—Internal force in the backbone expressed in global frame coordinates.
m(s): $\in \mathbb{R}^6$—Internal moment in the backbone expressed in global frame coordinates.
$f_e(s)$: $\in \mathbb{R}^6$—External force per unit s on the backbone expressed in global frame coordinates.
$l_e(s)$: $\in \mathbb{R}^6$—External moment per unit s on the backbone expressed in global frame coordinates.
$f_t(s)$: $\in \mathbb{R}^6$—Sum of all forces per unit s applied to the backbone by tendons, expressed in global frame coordinates.
$l_t(s)$: $\in \mathbb{R}^6$—Sum of all moments per unit s applied to the backbone by the tendons, expressed in global frame coordinates.
$f_i(s)$: $\in \mathbb{R}^6$—Force per unit s applied to the $i^{th}$ tendon by it surrounds.
$n_i(s)$: $\in \mathbb{R}^6$—Tension in the $i^{th}$ tendon.
$\tau_i$: $\in \mathbb{R}$—Tension in the $i^{th}$ tendon. It is constant along s under the frictionless assumption.

B. Derivation of $f_i(s)$
Beginning with (11), $$n_i = \tau_i \frac{\dot{p}_i}{\|\dot{p}_i\|},$$

one can re-arrange and differentiate to obtain $$\dot{p}_i = \frac{1}{\tau_i} \|\dot{p}_i\| n_i,$$

$$\ddot{p}_i = \frac{1}{\tau_i} \left( \frac{d}{ds} (\|\dot{p}_i\|) n_i + (\|\dot{p}_i\|) \dot{n}_i \right).$$

Noting that $n_i \times n_i = 0$, one can take a cross product of the two results above to find, $$\dot{p}_i \times \ddot{p}_i = \frac{\|\dot{p}_i\|^2}{\tau_i^2} (\dot{n}_i \times n_i)$$

and so $$\dot{p}_i \times (\ddot{p}_i \times \dot{p}_i) = \frac{\|\dot{p}_i\|^3}{\tau_i^3} (n_i \times (\dot{n}_i \times n_i)).$$

Applying the vector triple product identity, $a \times (b \times c) = b(a \cdot c) - c(a \cdot b)$, one can expand the right-hand side of this equation. Since $\tau_i$ (the magnitude of $n_i$) is constant with respect to s, then $n_i \cdot \dot{n}_i = 0$, and this results in $$f_i = -\dot{n}_i = -\tau_i \frac{\dot{p}_i \times (\ddot{p}_i \times \dot{p}_i)}{\|\dot{p}_i\|^3}.$$

Using the fact that $a \times b = -b \times a$, and writing the cross products in skew-symmetric matrix notation ($a \times b = \hat{a} b$), one arrives at $$f_i = \tau_i \frac{\dot{p}_i \times (\dot{p}_i \times \ddot{p}_i)}{\|\dot{p}_i\|^3} = \tau_i \frac{\hat{\dot{p}}_i^2}{\|\dot{p}_i\|^3} \ddot{p}_i.$$

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

For example, in some embodiments, the method described above can also be used to determine the load or external forces and moments being applied to the elastic support member. In such embodiments, the 3D shape of the elastic support member can be determined via some kind of sensing method (i.e., with cameras, or optical fibers, or magnetic tracking coils, or ultrasound, or fluoroscopy, etc.). Thereafter, using a known tension on the rod and routing path for the rod, the iterative model equations described above can be iteratively solved to determine the external forces and moments ($f_e$ and $l_e$) which result in the model-predicted shape that is close to the actual sensed shape. The resulting loads based on the model can then be used as an estimate of the loads acting on the elastic support member. Accordingly, these loads can be used to provide useful information to one who is operating the continuum robot. Alternatively, a similar method can be used to compute the required rod tension necessary to achieve forces and moments for the continuum robot to exert on its surroundings. In such embodiments, the 3D shape of the elastic support member is also determined via some kind of sensing method. Thereafter, the external loads are estimated using the above-mentioned procedure. Finally, the adjustment in tension needed to achieve a desired load or shape can be determined iteratively using the system of equations.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A device comprising:
    an elastic support member;
    at least one rod being pre-curved when no forces are applied to the device; and
    a plurality of support discs, each of the plurality of support discs forming a plurality of apertures, at least one of the plurality of apertures being adapted to receive one of the at least one rod,
    wherein material forming the at least one rod has a different stiffness than a stiffness of material forming the elastic support member, and
    wherein the elastic support member is attached to the plurality of support discs so as to maintain spacing between the plurality of support discs,
    wherein the at least one rod slidably extends along one of the plurality of apertures to position the plurality of support discs and forces the elastic support member to conform to a shape defined by a position of the at least one rod.

2. The device of claim 1, wherein the at least one rod has an elongated cross-section.

3. The device of claim 1, wherein the at least one rod has a cross-section being rectangular.

4. The device of claim 1, wherein one of the plurality of support discs is positioned at a first end of the device and a second one of the plurality of support discs is positioned at a second end of the device.

5. The device of claim 4, wherein the at least one rod is continuous between the plurality of support discs positioned respectively at the first and second ends of the device.

6. The device of claim 1, wherein the material forming the at least one rod comprises nitinol.

7. A device comprising:
    an elastic support member;
    a plurality of rods being pre-curved when no forces are applied to the device, each of the plurality of rods continuously extending from a first end of the device to a second end of the device; and
    a plurality of support discs, each of the plurality of support discs comprising a plurality of apertures located around a periphery thereof, at least one of the plurality of apertures being adapted to receive one of the plurality of rods,
    wherein material forming the plurality of rods has a different stiffness than a stiffness of material forming the elastic support member, and
    wherein the elastic support member is attached to the plurality of support discs so as to maintain spacing between the plurality of support discs,
    wherein the at least one rod slidably extends along one of the plurality of apertures to position the plurality of support guides and forces the elastic support member to conform to a shape defined by a position of the at least one rod.

8. The device of claim 7, wherein each of the plurality of rods has an elongated cross-section.

9. The device of claim 7, wherein each of the plurality of rods has a cross-section being rectangular.

10. The device of claim 7, wherein the material forming the at least one rod comprises nitinol.

* * * * *